(12) United States Patent
McKnight et al.

(10) Patent No.: US 8,993,327 B2
(45) Date of Patent: Mar. 31, 2015

(54) PARALLEL MACROMOLECULAR DELIVERY AND BIOCHEMICAL/ELECTROCHEMICAL INTERFACE TO CELLS EMPLOYING NANOSTRUCTURES

(75) Inventors: Timothy E. McKnight, Greenback, TN (US); Anatoli V. Melechko, Oak Ridge, TN (US); Guy D. Griffin, Oak Ridge, TN (US); Michael A. Guillorn, Knoxville, TN (US); Vladimir L. Merkulov, Knoxvill, TN (US); Michael L. Simpson, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1622 days.

(21) Appl. No.: 10/408,294

(22) Filed: Apr. 7, 2003

(65) Prior Publication Data

US 2004/0197909 A1    Oct. 7, 2004

(51) Int. Cl.
| | |
|---|---|
| C12N 15/00 | (2006.01) |
| C12N 15/88 | (2006.01) |
| C12N 15/87 | (2006.01) |
| C12N 15/82 | (2006.01) |
| C12N 15/74 | (2006.01) |
| A61K 48/00 | (2006.01) |
| C12N 11/00 | (2006.01) |

(Continued)

(52) U.S. Cl.
CPC . B82Y 5/00 (2013.01); C12N 11/00 (2013.01); C12N 11/06 (2013.01); *Y10S 977/732* (2013.01); *Y10S 977/734* (2013.01); *Y10S 977/742* (2013.01); *Y10S 977/746* (2013.01)
USPC ........... 435/440; 435/455; 435/458; 435/464; 435/470; 435/476; 977/732; 977/734; 977/742; 977/746; 514/44 R

(58) Field of Classification Search
None
See application file for complete search history.

(56) References Cited

U.S. PATENT DOCUMENTS

| | | | |
|---|---|---|---|
| 5,457,041 A | 10/1995 | Ginaven et al. | |
| 6,846,668 B1 * | 1/2005 | Garman et al. | ............ 435/285.1 |

(Continued)

FOREIGN PATENT DOCUMENTS

| | | | |
|---|---|---|---|
| JP | 2002-60680 | * | 3/2002 |
| WO | WO 00/20554 | | 4/2000 |
| WO | WO 01/67821 A1 | | 9/2001 |

OTHER PUBLICATIONS

Sotiropoulou et al., 2002/2003, Anal. Bioanal. Chem. 375:103-105.*

(Continued)

*Primary Examiner* — Robert M Kelly
*Assistant Examiner* — Kelaginamane T Hiriyanna
(74) *Attorney, Agent, or Firm* — Scully, Scott, Murphy & Presser, P.C.

(57) ABSTRACT

Systems and methods are described for parallel macromolecular delivery and biochemical/electrochemical interface to whole cells employing carbon nanostructures including nanofibers and nanotubes. A method includes providing a first material on at least a first portion of a first surface of a first tip of a first elongated carbon nanostructure; providing a second material on at least a second portion of a second surface of a second tip of a second elongated carbon nanostructure, the second elongated carbon nanostructure coupled to, and substantially parallel to, the first elongated carbon nanostructure; and penetrating a boundary of a biological sample with at least one member selected from the group consisting of the first tip and the second tip.

17 Claims, 14 Drawing Sheets

(51) Int. Cl.
B82Y 5/00 (2011.01)
C12N 11/06 (2006.01)

(56) References Cited

U.S. PATENT DOCUMENTS

| | | | |
|---|---|---|---|
| 2002/0084410 A1* | 7/2002 | Colbert et al. | 250/306 |
| 2002/0175323 A1 | 11/2002 | Guillom et al. | |
| 2002/0193729 A1 | 12/2002 | Cormier et al. | |
| 2003/0228695 A1* | 12/2003 | Nakamura et al. | 435/455 |
| 2004/0076681 A1* | 4/2004 | Dennis et al. | 424/489 |

OTHER PUBLICATIONS

Ren et al., 1998, Science 282:1105-1107.*
Cai et al., 2003, Anal. Bioanal. Chem. 3752:287-293.*
Wong et al., 1998, Nature 394:52-54.*
Li et al., 1996, Science 74: 17011703.*
Oupicky et al., (2002, JACS 124:8-9.*
Lemieux et al., 2000, J. Drug Target 8:91-105. (Abstract p. 1-2).*
Revzin et al., 2001, Langmuir 17:5440-7 (abstract p. 1).*
Hafner et al., 2001, Progress in Biophysics and Molecular Biology 77:73-110.*
Hu et al., 2002, J. Nanosci. Nanotech 2:203-207.*
Martin et al., 2002, Nature Reviews Drug Discovery 2:29-37.*
Endy, D., Brent R. 2001. *Modeling Cellular Behavior*. Nature. vol. 409. pp. 391-395.
Hasty, J., McMillen, D., Collins, J.J. *Engineered Gene Circuits*. Nature. vol. 420. Nov. 14, 2002. pp. 224-230.
Gardner, T.S., Cantor, C.R., Collins, J.J. *Construction of a Genetic Toggle Switch in Escherichia coli*. Nature. vol. 403. Jan. 20, 2000. pp. 339-342.
Elowtiz, M. B., Leibler, S. *A Synthetic Oscillatory Network of Transcriptional Regulators*. Nature. vol. 403. Jan. 20, 2000. pp. 335-338.
Guet, C.C., Elowtiz, M.B., Weihong, H., Leibler, S. *Combinatorial Synthesis of Genetic Networks*. Science. vol. 296 May 24, 2002. pp. 1466-1470.
Simpson, M.L., Sayler, G.S., Fleming, J.T., Applegate, B. *Whole-cell Biocomputing*. Trends in Biotechnology. vol. 19. No. 8. Aug. 2001. pp. 317-323.
Chan, W.C.W., Nie, S. *Quantum Dot Bioconjugates for Ultrasensitive Nonisotopic Detection*. Science. vol. 281. Sep. 25, 1998. pp. 2016-2018.
Bruchez, M. Jr., Moronne, M., Gin, P., Weiss, S., Alivisatos, A.P. *Semiconductor Nanocrystals as Fluorescent Biological Labels*. Science. vol. 281. Sep. 25, 1998. pp. 2013-2016.
Dubertret, B., Skourides, P., Norris, D.J., Noireaux, V., Brivanlou, A.H., Libchaber, A. *In Vivo Imaging of Quantum Dots Encapsulated in Phospholipid Micelles*. Science. vol. 298. Nov. 29, 2002. pp. 1759-1762.
Wightman, R.M., Jankowski, J.A., Kennedy, R.T., Kawagoe, K.T., Schreoder, T.J., Leszczyszyn, D.J., Near, J.A., Diliberto, E.J., Viveros, O.H. *Temporally Resolved Catecholamine Spikes Correspond to Single Vesicle Release from Individual Chromaffin Cells*. Proc. Natl. Acad. Sci. U.S.A. vol. 88. 1991. pp. 10754.
Knoblauch M., Hibberd, J. M., Gray, J. C., van Bel, A. J. E. *A Galinstan Expansion Femtosyringe for Microinjection of Eukaryotic Organelles and Prokaryotes*. Nature Biotechnology. vol. 17. Sep. 17, 1999. pp. 906-909.
McAllister, D.V., Allen, M.G., Prausnitz, M.R. *Microfabricated Microneedles for Gene and Drug Delivery*. Annu. Rev. Biomed. Eng. 2000. pp. 289-313.
Wong, S.S., Joselevich, E., Woolley, A.T., Cheung, C.L., Lieber, C.M. *Covalently Functionalized Nanotubes as Nonometresized Probes in Chemistry and Biology*. Nature. vol. 394. Jul. 2, 1998. pp. 52-55.
Wooley, A.T., Guillemette, C., Cheung, C.L, Housman, D.E., Lieber, C.M. *Direct Haplotyping of Kilobase-size DNA Using Carbon Nanotube Probes*. Nature Biotechnology. vol. 18. Jul. 2000. pp. 760-763.

Guillom, M.A., McKnight, T.E., Melechko, A., Merkulov, V.I., Britt, P.F., Austin, D.W., Lowndes, D.H., Simpson, M.L. *Individually Addressable Vertically Aligned Carbon Nanofiber-Based Electrochemical Probes*. Journal of Applied Physics. vol. 91. No. 6. Mar. 15, 2002. pp. 3824-3828.
Kim, P., Lieber, C.M. *Nanotube Nanotweezers*. Science. vol. 286. Dec. 10, 1999. pp. 2148-2150.
Ren, Z.F., Huang, Z.P., Xu, J.W., Wang, J.H., Bush, P., Siegal, M.P., Provencio, P.N. *Synthesis of Large Arrays of Well-Aligned Carbon Nanotubes on Glass*. Science. vol. 282. Nov. 6, 1998. pp. 1105-1107.
Merkulov, V.I., Lowndes, D.H., Wei, Y.Y., Eres, G. *Patterned Growth of Individual and Multiple Vertically Aligned Carbon Nanofibers*. Applied Physics Letters. vol. 76. No. 24. Jun. 12, 2000. pp. 3555-3557.
Merkulov, V.I., Guillom, M.A., Lowndes, D.H., Simpson, M.L. *Shaping Carbon Nanostructures by Controlling the Synthesis Process*. Applied Physics Letters. vol. 79. No. 8. Aug. 20, 2001. pp. 1178-1180.
Cong, B., Liu, J., Tanksley, S.D. *Natural Alleles at a Tomato Fruit Size Quantitative Trait Locus Differ by Heterochronic Regulatory Mutations*. PNAS. vol. 99. No. 21. Oct. 15, 2002. pp. 13606-13611.
Dwyer, C., Guthold, M., Falvo, M., Washburn, S., Superfine, R., Erie, D. *DNA-Functionalized Single-Walled Carbon Nanotubes*. Nanotechnology. vol. 13. 2002. pp. 601-604.
Nguyen, C.V., Delzeit, L., Cassell, A.M., Li, J., Han, J., Meyyappan, M. *Preparation of Nucleic Acid Functionalized Carbon Nanotube Arrays*. Nano Letters. vol. 2. No. 10. 2002. pp. 1079-1081.
Hsie, A.W., Casciano, D.A., Couch, D.B., Krahn, D.F., Oneill, J.P., Whitfield, B.L. *The Use of Chinese-Hamster Ovary Cells to Quantify Specific Locus Mutation and to Determine Mutagenicity of Chemicals—A Report of the Gene Tox Program*. Mutat. Res. vol. 86. pp. 193-214.
Merkulov, V.I., Melechko, A.V., Guillom, M.A., Lowndes, D.H., Simpson, M.L. Effects of Spatial Separation on the Growth of Vertically Aligned Carbon Nanofibers Produced by Plasma-Enhanced Chemical Vapor Deposition. Applied Physics Letters. vol. 80. No. 3. Jan. 21, 2002. pp. 476-478.
Brown, G.M., Allison, D.P., Warmack R.J., Jacobson, KB., Larimer, F.W., Woychik, R.P., Carrier, W.L. *Electrochemically Induced Adsorption of Radiolabelled DNA on Gold and HOPG Substrates for STM Investigations*. Ultramicroscopy. vol. 38. 1991. pp. 253-264.
Hamad-Schifferii, K, Schwartz, J.J., Stantos, A.T., Zhang, S., Jacobson, J.M. *Remote Electronic Control of DNA Hybridization Through Inductive Coupling to an Attached Metal Nanocrystal Antenna*. Nature. vol. 415. Jan. 10, 2002. pp. 152-155.
Luo, D., Staltzman, W.M. *Synthetic DNA Delivery Systems*. Nature Biotechnology. vol. 18. Jan. 2000. pp. 33-37.
Filion, M.C., Phillips, N.C., *Major Limitations in the Use of Cationic Liposomes for DNA Delivery*. International Journal of Pharm. vol. 162. 1998. pp. 159-170.
Merkulov, V.I., Melechko, A.V., Guillom, M.A., Lowndes, D.H., Simpson, M.L. *Alignment Mechanism of Carbon Nanofibers Produced by Plasma-Enhanced Chemical-Vapor Deposition*. Applied Physics Letters. vol. 79. No. 18. Oct. 29, 2001. pp. 2970-2972.
Arbault, S., Pantano, P., Sojic, N., Amatore, C., Best-Belpomme, M., Sarasin, A., Vuillaume, M. *Activation of the NADPH Oxidase in Human Fibroblasts by Mechanical Intrusion of a Single Cell with an Ultramicroelectrode*. Carcinogenesis. vol. 18. 1997. pp. 569-574.
Desai, T.A., Hansford, D. J., Ferrari, M. *Micromachined Interfaces: New Approaches in Cell Immunoisolation and Biomolecular Separation*. Biomolecular Engineering. vol. 17. 2000. pp. 23-36.
Merkulov, V.I., Lowndes, D.H., Baylor, L.R., Kang, S. *Field Emission Properties of Different Forms of Carbon*. Solid-State Electronics. vol. 45. 2001. pp. 949-956.
Ziauddin, J., Sabatini, D.M. *Microarrays of Cells Expressing Defined cDNAs*. Nature. vol. 411. May 3, 2001. pp. 107-110.
Merkulov, Vladimir I., Lowndes, Dourglas H., Baylor, Larry R., "Field-emission studies of smooth and nanostructure carbon films," Applied Physics Letters, vol. 75, No. 9, Aug. 30, 1999, pp. 1228-1230.
International Search Report and Written Opinion of the International Searching Authority, PCT/US2004/010512, Oct. 12, 2004.

* cited by examiner

BARE SILICON

FIBERED REGION

VERY LOW INCIDENCE OF
PI UPTAKE (~BACKGROUND)

FIBERED REGION | BARE SILICON | HIGH INCIDENCE OF PI UPTAKE IN FIBERED REGIONS

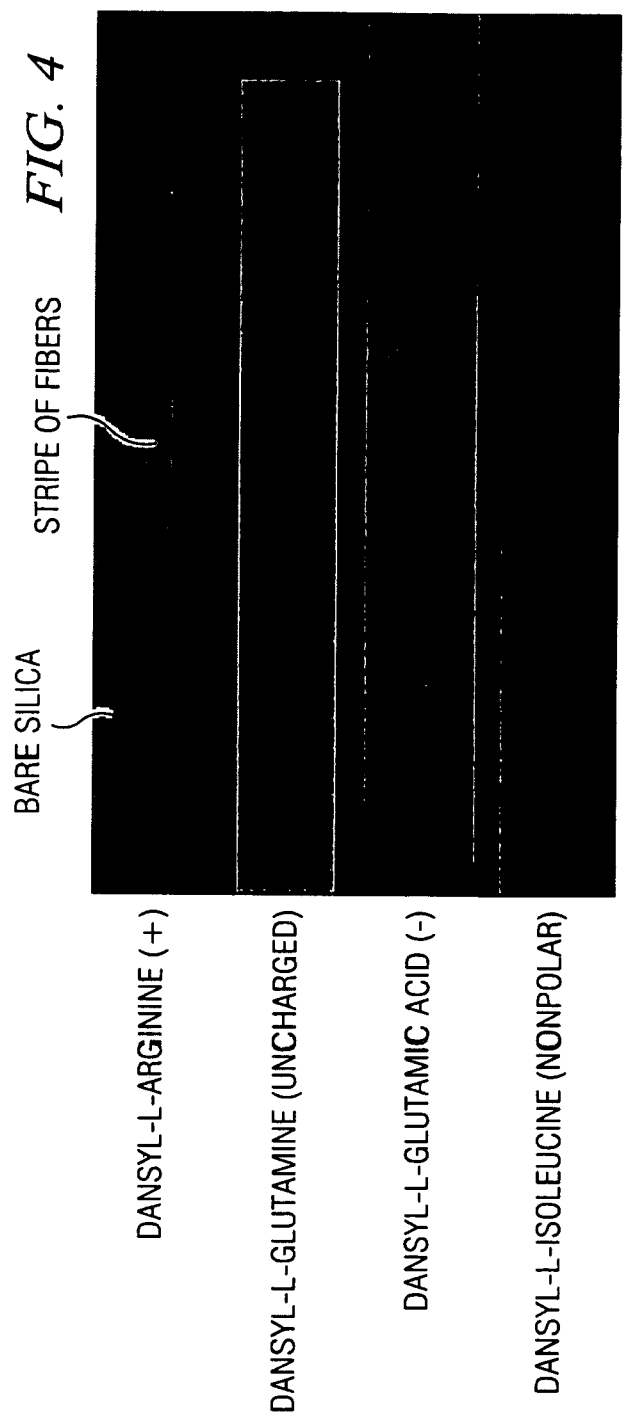

GEL ELECTROPHEROGRAM OF PLASMID DNA
INTERACTIONS WITH NANOFIBER SUBSTRATES

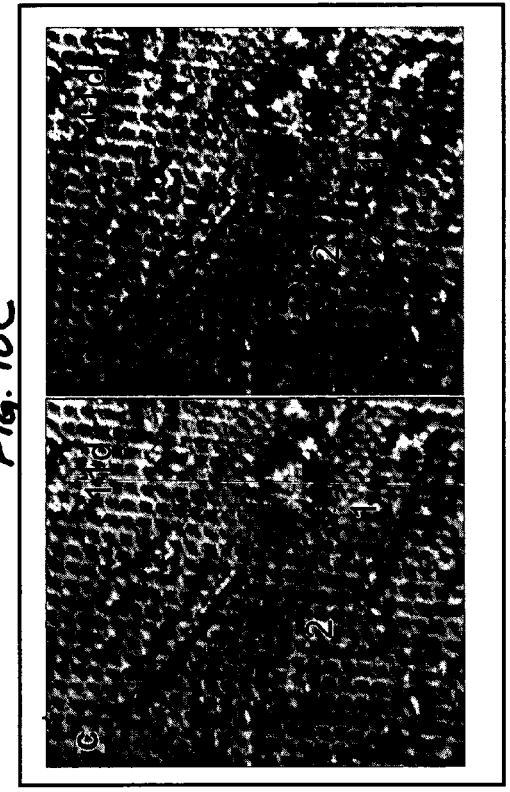
FIG. 10C
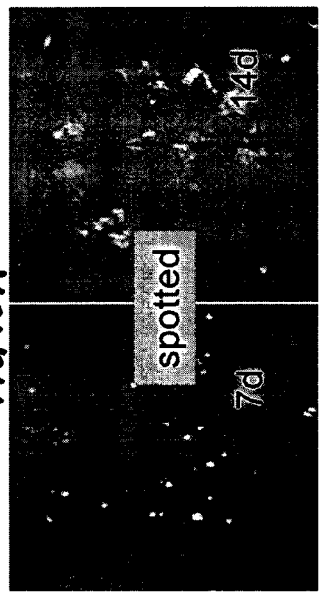
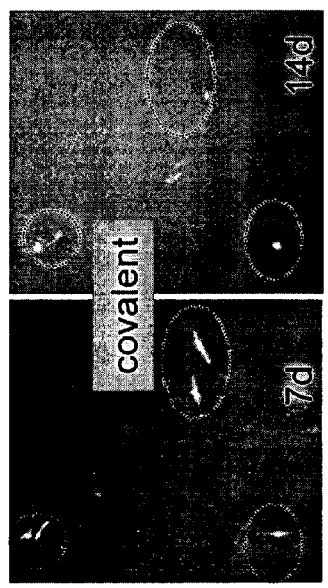
FIG. 10A
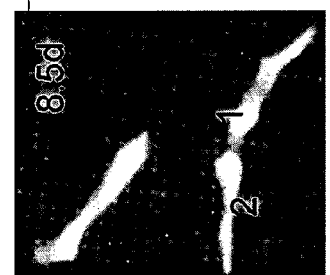
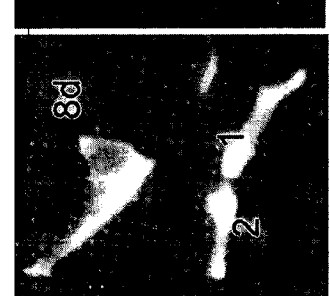
FIG. 10B

PARALLEL MACROMOLECULAR DELIVERY AND BIOCHEMICAL/ELECTROCHEMICAL INTERFACE TO CELLS EMPLOYING NANOSTRUCTURES

STATEMENT AS TO RIGHTS TO INVENTIONS MADE UNDER FEDERALLY-SPONSORED RESEARCH OR DEVELOPMENT

This invention was made with United States Government support under prime contract No. DE-AC05-00OR22725 to UT-Battelle, L.L.C. awarded by the Department of Energy. The Government has certain rights in this invention.

BACKGROUND OF THE INVENTION

1. Field of the Invention

The invention relates generally to the field of nanotechnology. More particularly, the invention relates to nanostructures, methods of preparing and interfacing nanostructures with biological systems, and devices for implementing such interfaces.

2. Discussion of the Related Art

Efficient manipulation of biological systems at the subcellular and, ultimately, molecular scale is a critical need to enable mankind to further its knowledge of cellular processes and to enhance our ability to modify and control cellular function. Much of the data on cellular processes were obtained by cell culture and study, where stimuli are applied to cells (chemical, electrical, electrochemical, thermal, mechanical, etc) and the cellular responses to stimuli are directly observed using a variety of techniques (microscopy, fluorimetry, electrochemistry, etc).

A variety of techniques exist for material delivery to live cells, particularly plasmid delivery. These methods are discussed and compared in the literature. A variety of techniques also exist for single element intracellular probing or material delivery, including traditional microinjection, pulled capillary or pulled fiber optic probes, and single carbon tube bundle electrophysiology. Parallel interfacing techniques also exist based largely upon culturing cells upon planar arrays of electrodes.

Often, research is conducted by observing a single specimen, or a single cell, at one time, applying a stimulus and observing a response. As the response of a single specimen may be dramatically different from the norm, many individual trials must be conducted to obtain information of normal response. Methodologies that would provide parallelism to such studies can significantly streamline effort and cost, and can dramatically improve the rate of knowledge gain.

Among the many methods that may be used to deliver DNA to a targeted cell, perhaps the most straightforward, but most effective, is microinjection—the direct administration of naked DNA to the intracellular domain of a targeted cell [27]. Microinjection forcibly bypasses the physical barriers that a cell relies upon to protect itself from foreign DNA, and in so doing, enables high probability for transformation success. Used routinely for eukaryotic transformation including both mammalian and plant cells, recent success with ultrafine micropipettes (<100 nm tip diameters) has been reported on prokaryotes and even targeted organelles [11]. The task of microinjection, however, is time consuming and arduous as the precision of the method requires the targeting of an individual cell and typically its nuclear envelope using fragile micropipettes and precise micromanipulators.

Parallel techniques for DNA delivery have naturally developed to streamline the process of engineering the cell. While the ultimate goal of these techniques is typically the delivery, stable insertion, and expression of exogenous DNA into a target organism, most methods typically only address one or two components of a complex, multistep process. As reviewed by Luo and Saltzman [27], once a cell is targeted, successful delivery requires that DNA breach the plasma membrane, run (or at least survive) the gauntlet of intracellular endosomal/lysosomal pathways, and (with some exceptions) pass yet another barrier, the nuclear envelope. Microinjection successfully addresses all of these components, including targeting of individual cells and subsequent breaching of the plasma and nuclear membrane, thereby eliminating the chance for cytosolic degradation of delivered vectors via endosomal/lysosomal pathways. In contrast to microinjection, very few methods target individual or select groups of cells, but instead approach DNA delivery as a bulk process. Electroporation, sonoporation, DNA complexing and/or precipitation, and microprojectile bombardment are all designed as bulk processes where a vector or multiplexed vectors are delivered to cells with little potential for targeting individual groups. Similarly, while viral mediated methods are highly efficient, and may be used to target specific cells or cell types, they provide no ability to target individual groups of cells within a cellular matrix. Whisker or fiber-mediated methods have also evolved that typically employ small DNA-coated fibers (carbon) or whiskers (silicon carbide) that are physically vortexed in suspensions of cells, causing localized abrasions and ultimately some unpatterned delivery to cells in the suspension. These latter methods have been typically targeted at plant cells that feature a rigid cell wall as an additional barrier to intracellular delivery.

In recent years, a large funding base directed towards gene therapy and pharmaceutical exploration combined with advances in microscale fabrication has focused a sector of the research community on developing devices and improved methods for delivering large molecules (drugs and genetic vectors) into intact cells and tissue. To date, many of these efforts have focused on the development of consumer-oriented drug-delivery platforms by utilizing the miniaturization afforded by microscale fabrication. Examples include arrays of microscale 'painless' needles for transdermal drug delivery [12] or microfabricated insulin vesicles that conceivably could interface with the bloodstream and provide insulin infusion when required [31].

While microscale technologies are and will continue to produce dramatic advances in biological and biomedical applications, the nanoscale, not the microscale, is the proper size regime for a direct interface to the molecular mechanisms of cells. McAllister's painless needle, an array of needles produced by reactive ion etching of silicon, features 100 micron long needles with tip diameters of microns. While these needles can effectively penetrate the stratum corneum (the dead outer layer of skin) and deliver material to the interstitial fluid and capillary beds of the epidermis, they are too large for direct material delivery into cells.

The research community has developed a variety of techniques for delivering large molecules into cells, and continues to actively seek new methods for both in-vitro (for laboratory research) and in-vivo (for clinical application) material delivery. Traditional methods rely on either natural biological mechanisms or coarse, mechanically-based means of disrupting the cellular envelope to enable passage of extracellular material. The biological methods, employing bacterial or viral infection as the transformation mechanism (i.e transfection), are only narrowly applicable, working selectively on organisms that act as hosts to the infective vector. The mechanical methods—including electro/sono/optoporation, silicon carbide whisker mediated delivery, microprojectile bombardment, and microinjection—operate on the principle of cellular envelope disruption or physically penetrating the membrane barrier. Except for microinjection, these methods are employed on bulk volumes of cells. While powerful (and sometimes highly efficient), these methods lack the highly parallel and site-specific delivery of molecular material to cells that is the key requirement for bringing powerful combinatorial techniques to the molecular manipulations of cells. As a result, research that investigates cellular response to a variety of different macromolecular reagents requires manipulating many different samples, isolation and culture of these individual samples, and careful practice to ensure samples are treated similarly (to enable true comparison of results between samples). Experiments evaluating a large array of different macromolecules to be delivered (such as gene delivery for the investigation of the functions of gene groups with single base polymorphisms) can quickly become overwhelming in terms of effort and cost. The tools the inventors propose here transform these serial operations into parallel—actually massively parallel—operations. Similar tools for combinatorial chemistry revolutionized therapeutic drug discovery and are making significant impacts in numerous other fields.

Recently, researchers at the Whitehead Institute have described a powerful new combinatorial-based approach that provides for spatially resolved cellular transformation of cultured mammalian cells [33]. In brief, cells are cultured directly onto microscope slides that have been prepared with isolated spotted regions of assorted plasmid DNAs immobilized within a gelatin matrix. Using a lipid transfection agent, discrete groups of cells grown upon these isolated regions are able to uptake, and express, the exogenous plasmid. While limited to a subset of mammalian cells that may be directly cultured and that directly uptake naked DNA, this combinatorial method has an enormous potential for rapidly screening large sets of cDNAs or DNA constructs by directly observing phenotypic changes of discrete regions of identically handled cells. Expanding upon the Whitehead study to provide a method for evaluating gene function using a larger variety of cell types (and possibly tissue) would dramatically strengthen the power of these combinatorial methods.

Microinjection is perhaps the most reliable tool for material delivery at the single cell level. As microinjection is simply using a microscale needle to penetrate the cellular barrier and deliver material, this technique is perhaps the most universally applicable method for a variety of different cell types. While implementation is technically challenging (requiring micromanipulation of pulled capillaries and cells under an optical microscope) and throughput is very low, delivery efficiency is typically very high on a cell to cell basis. A somewhat analogous method is used in bulk solutions, 'silicon carbide whisker mediated transformation'. Plasmid/cell suspensions are formulated with small amounts of silicon carbide whiskers (microscale needlelike fibers) that, when agitated, promote material delivery by creating lesions in the walls and membranes of cells.

SUMMARY OF THE INVENTION

There is a need for the following aspects of the invention. Of course, the invention is not limited to these aspects.

According to an aspect of the invention, a method, comprises providing a first material on at least a first portion of a first surface of a first tip of a first elongated carbon nanostructure; providing a second material on at least a second portion of a second surface of a second tip of a second elongated carbon nanostructure, the second elongated carbon nanostructure coupled to, and substantially parallel to, the first elongated carbon nanostructure; and penetrating a boundary of a biological sample with at least one member selected from the group consisting of the first tip and the second tip. According to another aspect of the invention, a method, comprises providing a material on at least a portion of a surface of a tip of an elongated carbon nanostructure; penetrating a boundary of a biological sample with the tip; and pressing the cell against a wetted substantially flat surface. According to another aspect of the invention, an apparatus, comprises at least one elongated carbon nanostructure including a tip, wherein the tip of the elongated carbon nanostructure includes a catalyst having an exposed portion, and wherein the exposed portion of the catalyst defines a localized handle for retention of a material. According to another aspect of the invention, an apparatus, comprises at least one elongated carbon nanostructure including a tip; and a metalization layer coupled to at least a portion of a surface of the tip of the elongated carbon nanostructure. According to another aspect of the invention, an apparatus, comprises at least one elongated carbon nanostructure including a tip; and a silicon containing oxide layer coupled to at least a portion of a surface of the tip of the elongated carbon nanostructure. According to another aspect of the invention, an apparatus, comprises at least one elongated carbon nanostructure including a tip; and a thermally reactive coating coupled to at least a portion of a surface of the tip of the elongated carbon nanostructure. According to another aspect of the invention, an apparatus, comprises at least one elongated carbon nanostructure including a tip; and DNA complexed to at least a portion of the tip of the carbon nanostructure. According to another aspect of the invention, an apparatus, comprises at least one elongated carbon nanostructure including a tip; and carboxylic acids coupled to at least a portion of a surface of the tip of the elongated carbon nanostructure. According to another aspect of the invention, an apparatus, comprises at least one elongated carbon nanostructure including a tip, wherein at least a portion of the tip of the elongated carbon nanostructure includes nitrogenated carbon. According to another aspect of the invention, a method, comprises providing at least one elongated carbon nanostructure including a tip, wherein the tip of the elongated carbon nanostructure includes a catalyst having an exposed portion, and wherein the exposed portion of the catalyst defines a localized handle for retention of a material. According to another aspect of the invention, a method, comprises providing at least one elongated carbon nanostructure including a tip; and forming a metalization layer coupled to at least a portion of a surface of the tip of the elongated carbon nanostructure. According to another aspect of the invention, a method, comprises providing at least one elongated carbon nanostructure including a tip; and forming a silicon containing oxide layer coupled to at least a portion of a surface of the tip of the elongated carbon nanostructure. According to another aspect of the invention, a method, comprises providing at least one elongated carbon nanostructure including a tip; and forming a thermally reactive coating coupled to at least a portion of a surface of the tip of the elongated carbon nanostructure. According to another aspect of the invention, a method, comprises providing at least one elongated carbon nanostructure including a tip; and complexing DNA to at least a portion of the tip of the carbon nanostructure. According to another aspect of the invention, a method, comprises providing at least one elongated carbon nanostructure including a tip; and forming carboxylic acids coupled to at least a portion of a surface of the tip of the elongated carbon nanostructure. According to another aspect of the invention, a method, comprises providing at least one elongated carbon nanostructure including a tip, wherein at least a portion of the tip of the elongated carbon nanostructure includes nitrogenated carbon synthesized from a plasma enhanced chemical vapor deposition with a carbonaceous source gas and a nitrogenated etch gas.

These, and other, aspects of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein identical reference numerals (if they occur in more than one view) designate the same elements. The invention may be better understood by reference to one or more of these drawings in combination with the description presented herein. It should be noted that the features illustrated in the drawings are not necessarily drawn to scale.

FIG. 4 illustrates preferential adsorption on surface treated carbon nanofibers, representing an embodiment of the invention.

FIGS. 10A-10C illustrate fluorescent micrographs of CHO cells expressing VACNF-delivered GFP plasmid (FIG. 10A) time-lapse images of GFP+ cells from (top) spotted (non-specifically adsorbed plasmid) nanofibers, and (bottom) nanofibers with covalently linked plasmid. The spotted samples tend to produce colonies of cells from initial transfectants while the covalently linked samples tend to maintain a constant number of GFP+ cells (FIG. 10B) a time-lapse sequence of a typical cell division on a covalently linked plasmid VACNF array indicating that plasmid DNA is not segregated to progeny cells (within one day after cell division, no fluorescence is observed from the daughter cell not retained on the nanofiber) (FIG. 10C) illustrates a brightfield image demonstrating that the daughter cell still resides adjacent to the mother cell. This division and subsequent loss of GFP expression in the daughter cells for covalently-linked plasmid VACNF samples maintains constant numbers of GFP+ cells over long periods of time, as indicated in the lower two panels of part FIG. 10A (scale bars=50 µm), representing an embodiment of the invention.

DESCRIPTION OF PREFERRED EMBODIMENTS

Figure 1:
FIG. 1 illustrates a scanning electron micrograph of a cell with an inserted carbon nanofiber, representing an embodiment of the invention.

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

Within this application several publications are referenced by Arabic numerals within parentheses. Full citations for these, and other, publications may be found at the end of the specification immediately preceding the claims after the section heading References. The disclosures of all these publications in their entireties are hereby expressly incorporated by reference herein for the purpose of indicating the background of the invention and illustrating the state of the art.

The below-referenced U.S. Patent Application(s) disclose embodiments that were satisfactory for the purposes for which they are intended. The entire contents of U.S. patent application Ser. No. 09/810,531, filed Mar. 15, 2001; Ser. No. 09/795,660, filed Feb. 27, 2001; Ser. No. 09/964,270, filed Sep. 26, 2001; Ser. No. 10/068,795, filed Feb. 6, 2002; and Ser. No. 10/155,841, filed May 24, 2002 are all hereby expressly incorporated by reference herein for all purposes.

The carbon nanofiber is of a size scale appropriate for interaction with live cells. With nanometer radii and micron lengths, its size is appropriate for insertion into the intracellular domain of many cell types (similar to microcapillaries and microscale probes utilized for microinjection and probing of living cells). The carbon nanofiber may be synthesized with an exceptional degree of control, tailoring the physical properties of size, location on a substrate, and chemical composition. Using a plasma-enhanced chemical vapor deposition (PECVD) process, carbon nanofibers may be synthesized at specific locations upon a substrate as defined by the lithographic patterning of catalyst metals, such as Ni, Co, and Fe. In the first step of the PECVD process, catalyst material is nucleated from a thin film on the substrate into nanoscale droplets. During subsequent fiber growth, each catalyst droplet precipitates the deposition of carbon from the gas phase, forming a carbon fiber. Based upon growth parameters, the resultant structure may be a chaotic winding of carbonaceous material (base-growth) or may result in highly aligned, vertically-oriented fibers that grow perpendicular to the substrate (tip-growth) [29]. The mechanisms of tip-growth provide a high degree of control over the ultimate shape of vertically-aligned nanofibers, including ultimate fiber length, tip diameter, and geometry (conicity) [19]. Typically, nanofibers may be grown several microns in length, with tip diameters as small as tens of nanometers. In addition to geometry, surface chemistry (and surface charge) may also be tailored by adjusting the ratio of the carbonaceous source gas and an etchant gas, which is introduced to the plasma process during fiber growth.

The high aspect ratio of carbon nanofibers, their small nanoscale tips, and the ability to synthesize these nanoscale elements at defined locations, enable them to be implemented in systems that integrate with whole cells and cellular matrices. Further, the ability to synthesize vertically-aligned nanofibers in parallel arrays, provides basis for integrating many fibers with cells in a parallel manner.

The invention can include the integration, retention, and assimilation of carbon nanofiber arrays with the intracellular domains of mammalian cells to provide a device and methodology for macromolecular delivery and parallel interfacing to large numbers of viable cells. Suspensions of cells can be pelleted using centrifugation onto vertically-aligned carbon nanofiber arrays, resulting in impalement of some cells with nanofiber elements. The number of cells impaled may then be increased by pressing the nanofiber substrate against a wetted flat surface, with the pelleted cell layer sandwiched between the nanofiber substrate and the flat surface.

The invention can include the integration of these fibered substrates with the intracellular domains of cells via the delivery and expression of plasmid DNA, using the carbon nanofiber array as a material delivery vector (DNA adsorbed onto fibers are desorbed into intracellular domain) and as a plasmid scaffold that is assimilated into the cell's processes (DNA is covalently bound to fibers and transcribed for extended periods while attached to the nanofiber scaffold). The invention can include the use of nanofiber arrays as biochemical and electrochemical interfaces that may be integrated (inserted, retained, and assimilated) with living cells for extended periods for the purpose of interrogating, modifying, or controlling cellular function.

The invention can include parallel interfacing with whole cell matrices. This interfacing can involve the application of carbon nanofiber arrays as an instrument for parallel intracellular integration with cellular matrices.

The invention can include parallel delivery of DNA to cellular matrices, where DNA is delivered to many cells in parallel by direct insertion of DNA coated or DNA derivitized nanofibers into the intracellular domains of cells. The invention can include the integration of nanofiber arrays (insertion, retention, and assimilation) to produce a biochemical change within the targeted cells (i.e. the introduction of a new gene to the cell). In like manner, the invention can include the integration of nanofiber arrays with cells to produce other biochemical changes within the cell (delivery of other new molecules, removal of cellular molecules (though adsorption processes). The invention can include the use of nanofiber arrays to provide other stimuli to cells, including thermal (heat conduction through substrate, or radiative), electrical (via discrete or common leads on the nanofiber substrate), electrochemical (via discrete or common leads on the nanofiber substrate), and mechanical (insertion, vibrational, etc). The invention can also include the use of assimilated nanofiber arrays to transduce chemical, biochemical, electrochemical responses within the cell (e.g., as a redox electrode, or as an impedance probe of species adsorption, or as an impedance probe to specific ligand-receptor interactions). A preferred embodiment of the invention includes DNA delivery—or the biochemical modification of interfaced cells.

The invention, in contrast to the serial limitations of microinjection, provides the ability to grow vast arrays of nanofibers and to potentially integrate these devices with cellular matrices in a parallel fashion provides a parallel, microinjection-inspired, delivery scheme. The invention can include, for biochemical modification of interfaced cells, nanofiber arrays that are surface coated with plasmid vectors and directly integrated with cellular matrices. The transfer mechanism is a direct penetration and introduction of plasmid material simultaneously into many cells. Like microinjection, this approach has the potential of being very efficient as the nuclear domain can be targeted for material delivery (for eukaryotic cells). Also, like microinjection and suspension-based whisker- and fiber-mediated delivery techniques, this method may be suitable for a wide range of cell types, including both adherent and suspension cultures, tissue, and possibly plant, yeast, and prokaryotic cells, which feature the additional barrier of the cell well. However, in addition to simply providing parallelism to microinjection, nanofiber array vectors provide another unique, and perhaps even more significant aspect to physical delivery. Unlike larger single element microinjection systems, which typically must be carefully inserted into a cell, dispensed, and then removed, the size and substrate growth of nanofibers enables them to be integrated with cellular matrices and then left in place (i.e retained and assimilated). As such, material might be slowly released from the penetrant nanofiber scaffold into the intracellular domain. Material can also be covalently linked to the nanofiber scaffold and used for even longer intervals by the cell—perhaps being afforded some amount of protection from degradation due to the steric hindrances imposed by the scaffolding structure. As plasmid structures typically contain large portions of DNA that are unused by the cell, these areas can be used for fiber linkage while the used portions are accessible for polymerase activity and transcription. This capability has significant advantages in whole-cell biosensor applications that are often restricted in use due to the potential for release of genetic material to the environment (through plasmid replication, segregation, genomic insertion and propagation, and (in bacterial systems) plasmid dissemination. Scaffolding the plasmid DNA can reduce the potential for release as the tendency for genomic insertion (via crossing over and transposition) and plasmid dissemination (via replication, conjugation, and other lateral transfer mechanisms) can be diminished due to the physical attachment of the DNA with the scaffold and associated steric hindrances to replication and crossing-over mechanisms. This scaffolding can also provide an approach to controlling the expression of the plasmid. For example, transcription can be halted by physically removing the fiber and tethered plasmid from the cell or modulated by application of stimuli (electrical or electrochemical) to alter polymerase access to the bound plasmid.

The invention can include parallel intracellular integration. The invention can include parallel interfacing to cellular matrices. The invention can include intracellular interfacing. The invention can include electrically addressable structures. Nanofibers may be utilized as a stimulus (thermal, mechanical, electrical, chemical) or to measure response (electrochemical).

It is important to appreciate that the invention provides rich surface chemistries. The carbon nanostructure (e.g., nanofiber and/or nanotube) can be thought of as a very large organic molecule construct; a construct featuring many types of functional groups that may be modified by organic chemistry reactions. As they feature rich surface chemistries (carboxy, carboxylic acid, hydroxy, quinone, amine groups), a variety of derivitization chemistries may be employed to modify the surface of fiber with large and small molecules. Additionally, the fiber may be physically coated with other material, enabling other attachment chemistries. The inventors have demonstrated PECVD oxide coating followed by MAPTOS/pNIPAM (poly n isopropyl acrylamide). The inventors have also demonstrated metallization via sputtering, physical vapor deposition, and electroplating. The inventors have also demonstrated electrochemical polymerization coating with parylene.

Fiber arrays may be grown on any type of substrate (conductive, nonconductive, opaque, transparent) that can survive the PECVD growth process (700 deg C.). Typical substrates are silicon and quartz (fused silica).

While a preferred embodiment of the invention includes parallel nanostructures, the invention can include individual nanostructure elements as individual devices. Similarly, while a preferred embodiment of the invention includes intracellular integration of the devices, the invention can include nanofiber arrays implemented with cellular matrices, intercellularly, and in tissue interstitially and/or in intracellular/extracellular combinations.

The inventors have demonstrated GFP expression (and thus fiber integration) by simply pressing fibered substrates into tissue cultures. This technique could also be applied for integration of fibers directly with tissue in-situ, provided the fibers are of a length long-enough to reach regions of viable cells (i.e. the stratum corneum of human epithelial layers is several microns thick).

The inventors have presented nanofibers as a biochemical interface (coated and derivitized with DNA). The nanofibers may also be integrated with cellular matrices as an electrical interface or as an electrochemical interface. Similarly, the nanofiber array may be utilized as a thermal and mechanical interface, such as by conduction of heat through the substrate, or adsorption of radiation based upon adsorbance of the fibers.

The carbon nanofiber is mechanically robust—featuring a bamboo-like core of sequentially capped graphene structures and a surface coating of typically carbonaceous and sometimes nitrogenated material. In a series of experiments, The inventors investigated the interaction of vertically-aligned arrays of nanofibers with biological material. Initially, suspended Chinese hamster ovary (CHO) cells were centrifuged down onto vertically-aligned carbon nanofibers grown from nickel catalysts that were lithographically defined on a silicon substrate. This centrifugation was performed in a swinging-arm centrifuge at 100 G, such that the fibered substrate was oriented normal to the centrifugal force and thus vertical fibers were aligned with the pelleting force of centrifuged cells. The fibers of this substrate were patterned such that forests of fibers were grown in discrete lines 3 μm in width and many microns in length. Following 10 minutes of centrifugation, the cells that were pelleted onto the nanofiber array substrate were fixed in 2% paraformaldehyde/2% glutaraldehyde and subjected to methanol dehydration. Cells and substrate were then sputter coated with gold and cryogenically frozen for inspection using scanning electron microscopy. The resultant images indicated that most CHO cells had impacted forested regions of fibers and had apparently flattened. The fibers in these regions remained relatively unchanged, unbroken and unbent. In local regions, however, CHO cells could be found that had apparently interacted with the edges of fibered regions. In their centrifugal path to the substrate floor, these cells had apparently rotated over the edge of fibered regions and plucked fibers from the substrate with torsional force. Referring to FIG. 1, these fibers appeared to be penetrating the membranes of the cells, and relatively intact, except for the fact that they had been plucked from the substrate. These cells appeared to maintain their spherical (unattached) morphology—and thus did not appear deflated nor lysed due to the interaction.

In these centrifugation tests of fiber robustness, it appeared that some fibers were penetrating the membrane of spun CHO cells. To further study membrane penetration, cells were centrifuged onto fibers in the presence of a fluorogenic dye, propidium iodide. Propidium iodide (PI) is a DNA/RNA intercalator that exhibits a marked increase in quantum yield upon intercalation. It is a membrane impermeant dye, and therefore does not enter a cell unless the membrane is compromised such as due to stress, necrosis, or purposeful fiber-mediated penetration. Combined with its increase in quantum yield upon intercalation, these properties make PI well-suited for fluorescent studies of membrane integrity.

Figure 2A:
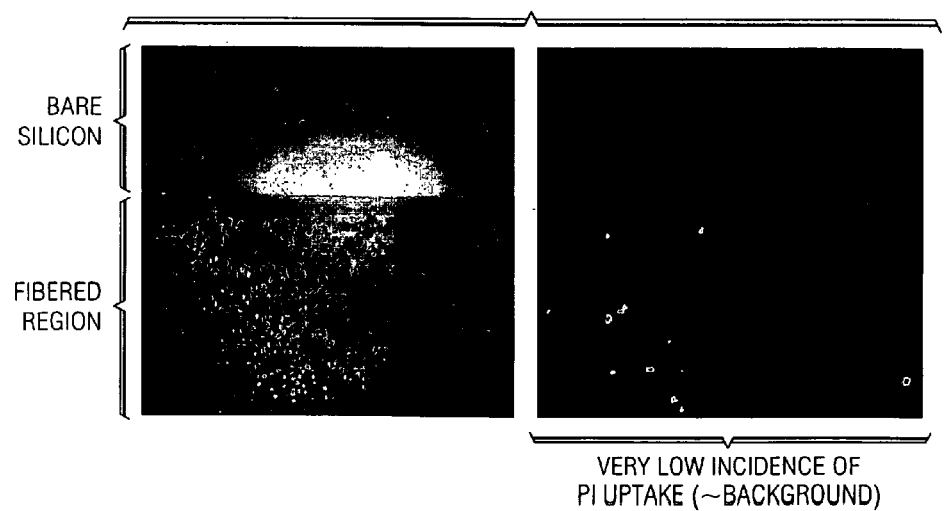
FIGS. 2A-2B illustrate cells (CHO, Jurkat, and the yeast *Pichia pastoris*) centrifuged down onto fibered substrates both (FIG. 2B) in the presence of 1 µM PI and (FIG. 2A) without PI (for the latter, PI was added five minutes following the spin), representing an embodiment of the invention.
Figure 2B:
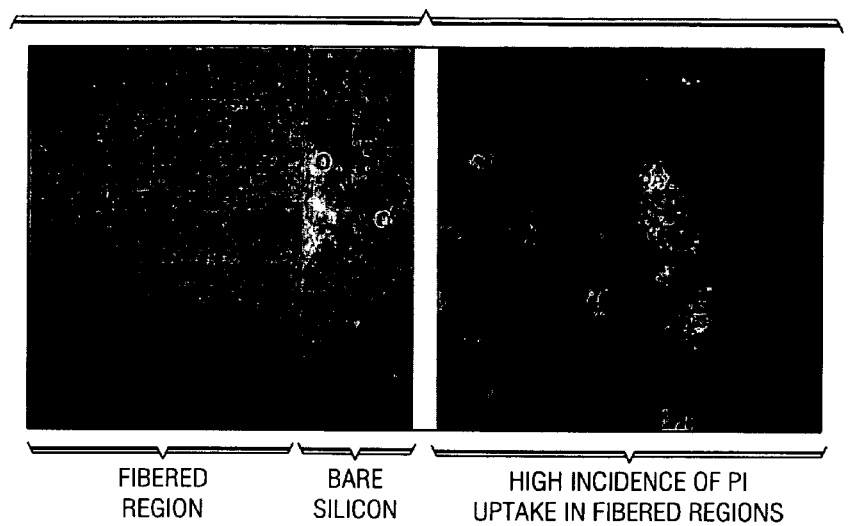

Referring to FIGS. 2A-2B, cells (CHO, Jurkat, and the yeast *Pichia pastoris*) were centrifuged down onto fibered substrates both in the presence of 1 μM PI and without PI. For the latter, PI was be added five minutes following the spin to evaluate if the putative penetrated membrane could reseal following the penetration event. For the mammalian cell lines, if fibered substrates were sparsely populated with fibers (such that one cell only experienced interactions with a few fibers) or featured a few long fibers per cell in a field of shorter fibers, fluorescent inspection of cells with a TRITC filter set indicated that cells were taking up PI—apparently due to fiber-mediated membrane compromise and, potentially, fiber penetration. Adding PI to centrifuged cells five minutes after the spinning resulted in considerably less PI uptake (approximately the same amount as uncentrifuged cells, i.e. normal necrosis of cells in culture), indicating that cells were apparently resealing around fibers, enabling them to exclude the impermeant PI dye. In these experiments, successful PI uptake required long fibers, with fiber lengths approximately equal to or greater than the diameter of cells (~7 µm). Cells spun onto lawns of short fibers (<2 µm) did not indicate membrane penetration, even at centrifugal forces of 10,000× G. However, these cells could be forced to take up PI by simply pressing the cell-covered fiber surface against a wetted flat surface (such as a microscope slide or the bottom of a culture dish) following the pelleting step. *Pichia pastoris*, a eukaryotic yeast often used as a protein expression system, indicated putative fiber-mediated uptake of PI using only centrifugation. This PI uptake, similar to the mammalian systems, could be increased by pressing the pelleted substrate against a wetted flat surface. This uptake was indicated using both osmotically-balanced (in 1 M Sorbitol) and unbalanced (in water) Pichia, potentially indicating that this penetration and delivery can be successfully implemented even in high osmotic pressured cell lines (i.e. plant cells, bacterial cells, yeast cells that have not been osmotically balanced with their suspension solution).

In a subsequent set of experiments, cells were centrifuged and cultured directly on fibered substrates. On both densely fibered substrates (>50 fibers/cell) and sparsely populated substrates (few fibers per cell), CHO and the mouse monocyte, J774a.1, were able to propagate successfully using the untreated fiber as an adhesion surface. Cell morphology was different from culture on traditional surfaces (treated polystyrene and glass). If fiber sizes were too large, cells could often be impaled, but apparently unable to attach and spread. It was not determined whether these cells were dying, but in subsequent experiments transfection of these cells and expression of GFP did indicate survival long enough to express off of delivered plasmid. While colony count assays have not been performed for the adherent cell lines, a study of proliferation of Jurkat (human acute lymphocytic suspension line) spun onto fibers at 50-200×G and subsequently resuspended indicated no appreciable decline in growth rate.

Traditional microinjection strategies physically deliver DNA into the intracellular domain via dispensing from a hollow capillary. Microprojectile bombardment, fiber- and whisker-mediated methods rely on shedding of adsorbed DNA from the solid element into and around abraded cells. Following this latter strategy, The invention can include successful macromolecular delivery using vertically-aligned-fiber-mediated methods where the molecules are adsorbed on the fiber surface and loosely retained such that they are shed in the intracellular domain. In the PI studies of cell penetration, the PI molecules were distributed within the cell suspension, and were thus available for uptake into the cell due merely to local compromise of the membrane. For spatially discrete plasmid delivery, the plasmid should be retained well by the fiber and only shed when subject to the intracellular domain. The inventors investigated a variety of coating methods to provide this adsorption, retention, and desorption. Based on a lipofection-based study, The inventors initially experimented with suspensions of plasmid in dilute solutions of agarose (0.1%), but also experimented with a variety of surface coatings on the fiber (sputtered gold, plasma enhanced chemical vapor deposited $SiO_2$), thermally reactive coatings (poly-n-isopropyl acrylamide, or pNIPAM), and DNA complexing agents (spermidine and $CaCl_2$ precipitation). Plasmids and plasmid cocktails were spotted directly onto fibered substrates with a micropipettor. Plasmid retention on fibers was evaluated qualitatively by staining the fibered substrates with propidium iodide and observing the degradation of fluorescence of fibered regions over time when immersed in aqueous buffers. In general, the agarose method provides a very diverse coating methodology, relatively independent of the surface charge effects that often limit DNA/surface interactions.

Figure 3:
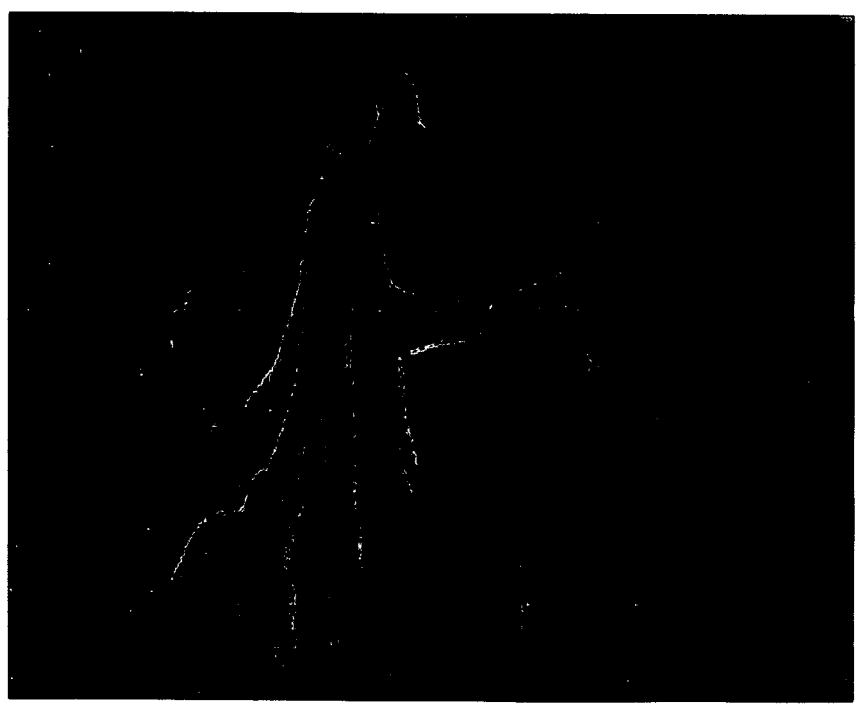
FIG. 3 illustrates DNA coupled to a plurality of carbon nanofibers, representing an embodiment of the invention.

Referring to FIG. 3, dried spots of DNA in 0.1% agarose provide fairly uniform coating of fibered surfaces, and only slightly diminish the high-aspect feature of the nanofibers in the dehydrated state. The agarose provides a slow release of the DNA from the fiber surface. Unfortunately, the presence of agarose on fibers during interaction and penetration of fibers into cells appears to considerably stress some cell lines—resulting in poor attachment, poor subsequent growth and markedly different morphology. It is unclear if this is a cytotoxic effect of the agarose, or merely an artifact of the ability of the cell to reseal following interaction with an agarose coated fiber. Hydration of the agarose matrix may also dramatically limit fiber penetration into cells due to swelling of the coated fiber.

Referring to FIG. 4, surface treatments of fibers can also appreciably affect DNA retention. In general, the native carbon nanofiber is a negatively charged surface, as indicated by fluorescent microscopy studies of the differential adsorption of fluorescently labeled (dansyl) amino acids: arginine, glutamine, glutamic acid, and isoleucine—where positively charged arginine resulted in increased fiber fluorescence due to preferential adsorption while the negatively charged, uncharged, and nonpolar amino acids tended to not accumulate appreciably on the fibers. The negatively charged carbon nanofiber surface will tend to electrostatically repel the anionic phosphate backbone of non-complexed DNA in dilute solutions. While such dilute solutions of DNA will coat fibers upon evaporation, they will quickly be shed upon rewetting of the sample. This is unacceptable for material delivery purposes, as plasmid vectors will be lost to solution upon wetting with the cellular suspension. However, this repulsive effect can be decreased by complexing the DNA with cations (i.e., Ca++) or cationic agents (spermidine), or by modifying the surface charge of the fiber with coatings—such as a sputtered gold or tungsten. Additionally, a wealth of silanization chemistries can be employed to modify the fiber surface if it is first coated with $SiO_2$. The invention can include very thin conformal coating of fibers (<50 nm) with $SiO_2$ using a plasma enhanced chemical vapor deposition process. This silica may then be modified using a polymerization procedure of acrylimide and the thermally-responsive p-n-isopropyl acrylamide onto a MAPTOS linkage group on the silica. This results in a hydrogel coating of the fibers at temperatures <30 deg C. that collapses to exclude water at a transition temperature at approximately mammalian incubator temperatures (37 deg C.). This strategy can be implemented as a controlled vector release that excludes the hydrated plasmid upon incubation following the spin-down of cells onto fibers.

In addition to these surface treatments, DNA may be complexed to fiber surfaces using a variety of techniques that have been developed in the microprojectile bombardment community, where plasmid coated microprojectiles are physically accelerated onto plates of recipient cells. In these methods, DNA is typically complexed to the particle using a cationic lipofective reagent (i.e. spermidine), and a highly concentrated precipitant ($CaCl_2$). Of all the methods employed, metallization of fibers resulted in the best retention of plasmid DNA on native carbon nanofibers.

Finally, in addition to post synthesis modification of carbon nanofibers, the fibers themselves may be synthesized with higher nitrogen content by simply altering the ratio of the carbonaceous source gas and the nitrogenated etch gas during PECVD synthesis. Highly nitrogenated fibers may be synthesized that bear an overall positive charge in physiological buffers, and thus electrostatically retain plasmid DNA without requiring any subsequent processing steps.

Figure 5A:
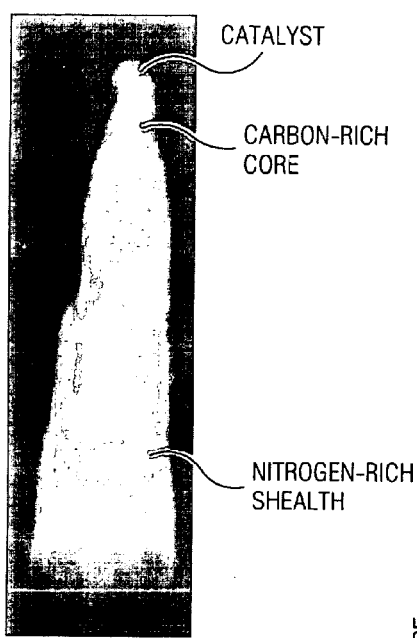
FIGS. 5A-5C illustrate preferential adsorption of 50 nm polystyrene latex beads to (FIG. 5B) an exposed portion of a nickel catalyst particle proximal an etched nanofiber tip but not on (FIG. 5C) the tip of a nanofiber that has not been etched to expose the nickel, representing an embodiment of the invention.
Figures 5B, 5C:
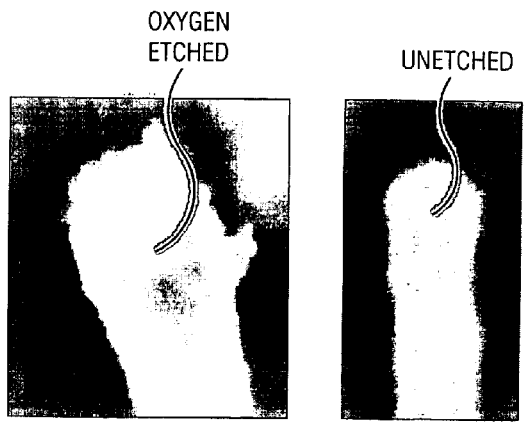

Ultimately, for effective material delivery, the material spotted onto a fiber array must breach the membrane barrier of the cell and be introduced to the intracellular domain. As such, the most important region of the fiber is that which will most likely enter the intracellular domain—the extreme tip. Careful inspection of a catalytically synthesized, tip-growth nanofiber reveals several important features relevant to material delivery applications. First, the tip of the fiber will typically contain a small amount of catalyst material. This material is sputtered during fiber growth, shrinking in size as the fiber grows. Ultimately, the PECVD growth process will completely sputter away the catalyst material. However, with careful control of the process, growth may be halted enabling the retention of some catalyst at the fiber tip. This catalyst will typically lay beneath thin layer of graphitic carbon (nm in thickness). If this carbon is removed, however, the metal catalyst particle may be exposed and used as a highly localized handle for DNA retention. This effect of exposing the catalyst particle is demonstrated in FIGS. 5A-5C, where 50 nm polystyrene latex beads are preferentially adsorbed to the exposed nickel of an oxygen etched fiber (see FIG. 5B) but not on the tip of a fiber that has not been etched to expose the nickel (see FIG. 5C).

Another feature of nanofiber tips is a short (~100 nm long) segment below the catalyst consisting almost entirely of carbon. Elemental analysis (EDX—energy dispersive x-ray analysis) reveals that even with a highly nitrogenated source gas mixture (which will produce heavily nitrogen doped fibers) the extreme tip of the fiber will be virtually nitrogen free. Modification of this region can thus provide another effective handle for DNA retention. One technique is the modification of carbon-rich regions with an oxygen plasma that produces oxide moieties, including carboxylic acids. With these handles, DNA may be covalently bound to the fibers using an EDC-mediated (1-ethyl-3-(3-dimethylaminopropyl)carbodiimide) condensation reaction between the fiber carboxylic acids and the DNA base amines.

Figure 6A:
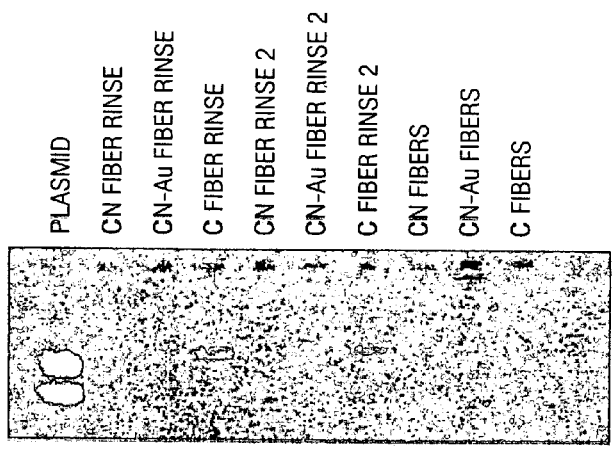
FIGS. 6A-6C illustrates laboratory results, representing an embodiment of the invention.
Figure 6B:
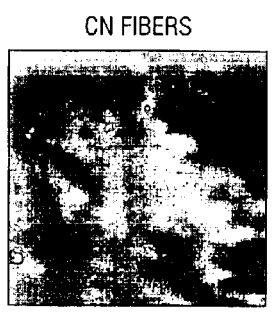
Figure 6C:
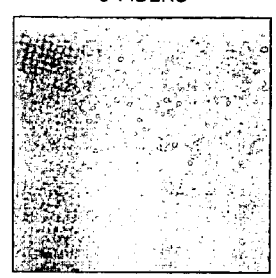

Delivery and expression of GFP coding plasmids following cell integration with nanofiber arrays is highly dependent on a number of factors including fiber geometry (length and diameter), spacing, and chemistry. In general, untreated carbon fibers were not successful with plasmid delivery. However, nitrogen containing fibers, exposed catalyst fibers, and plasmid derivitized (covalent) fibers all provided some amount of GFP+ expression in targeted cells. The failure of untreated carbon fibers appears to be due to poor retention of DNA on the fiber surface. Gel electrophoresis of DNA-coated fiber rinsate, fibers, and fiber substrates indicate that plasmid DNA is easily removed from the native carbon surface, and thus is likely not retained during cellular penetration events. Referring to FIG. 6A, it is apparently held more tightly to nitrogen containing fibers, and fibers that have been modified with metals via physical vapor deposition or electroplating. Referring to FIG. 6C, fluorescent studies of PI-labeled DNA spotted onto fibers also indicates removal of DNA from carbon fibers with aqueous rinsing. Referring to FIG. 6B, similar studies with nitrogen bearing fibers indicates that DNA cannot easily be rinsed off these fibers, but can be electrostatically pulled off fibers using gel-electrophoresis of fibers and fiber substrates at moderate field-strengths (100 V/cm)—where fibers are retained in wells of the electrophoresis gel, but DNA is pulled off the fibers and into the gel matrix.

Figure 7A:
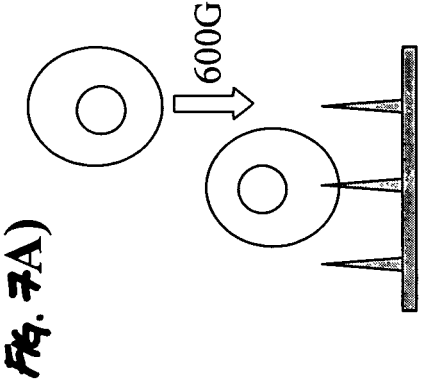
FIG. 7A illustrates when cells are spun out of a suspension in PBS onto a VACNF substrate, representing an embodiment of the invention.
Figure 7B:
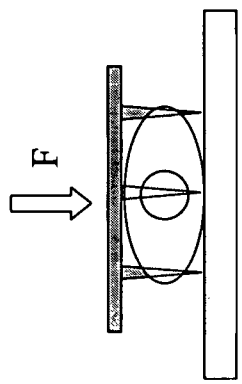
FIG. 7B illustrates that, following the spin of FIG. 7A, the substrate may be pressed against a wetted, flat surface, representing an embodiment of the invention.
Figure 7C:
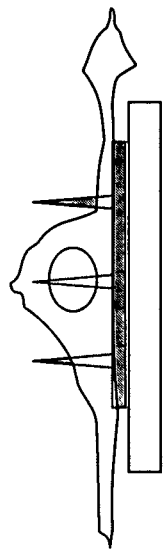
FIG. 7C illustrates a cell covered substrate placed face up in a culture dish, covered with growth media, and incubated for at least 24 hours prior to fluorescent imaging, representing an embodiment of the invention.

Referring to FIGS. 7A-7C, a laboratory use of the invention will now be described. Referring to FIG. 7A, centrifugation of cells at 3000 RPM (600 G) for 1 minute onto plasmid coated and plasmid derivitized nitrogen-bearing fibers results in transient expression of green fluorescent protein in CHO at efficiencies of approximately 1% (where efficiency is defined at GFP+ cells versus total number of cells on the fibered substrate). Referring to FIG. 7B, these efficiencies are improved by approximately a factor of 5 if, following the spin, the cell/fiber matrix is pressed lightly against a substantially flat, wetted surface such as a microscope slide or the bottom of a tissue culture dish. Efficiencies with fibers that had been spotted with DNA after emancipating the nickel catalyst at the tip were higher yet when using this spin and press method, with typically 20-50% of cells on the substrate expressing GFP during subsequent evaluations 24+ hours following the transfection experiment. In each of these scenarios, transfection efficiency is based on GFP+ cells versus total cells on the fibered substrate, and not GFP+ cells versus total number of cells spun down during the experiment. The efficiency of GFP expression from covalently linked plasmid-fiber arrays is highly dependent on the concentration of plasmid in the reaction mix. FIG. 7C shows the chip (substrate with a plurality of carbon nanostructures) carrying the impaled cell placed in growth media in a culture dish and incubated to allow cell recovery and proliferation.

Figure 8:
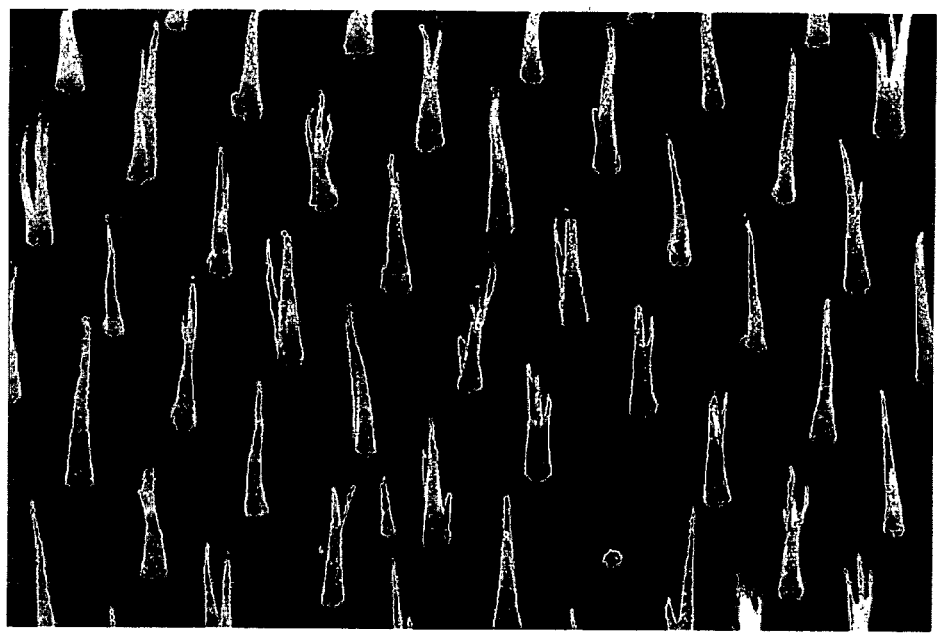
FIG. 8 illustrates a carbon nanofiber array lithographically defined and synthesized in a plasma enhanced chemical vapor deposition (PECVD) process featuring 5 µm spaced, 7 µm tall fibers with tip diameters of 30 nm (scale bar=5 µm), representing an embodiment of the invention.

Referring to FIG. 8, a 5×3 mm fiber array (with 7 micron fibers at 5 micron intervals) will result in a ~1% transfection rate using the spin and press methodology if 1 μg of plasmid DNA is covalently linked to the fibers in 1 ml of MES reaction buffer with 20 mg of EDC in the reaction mix. This same array will provide a 10-30% transfection rate if the reaction volume of MES is decreased to 0.3 mL. This indicates that the integration rate of fibers with cells is actually much higher than that indicated by plasmid delivery and expression, and is dependent upon integrated fibers having plasmid DNA available for transcriptional activity within the cell.

Figure 9:
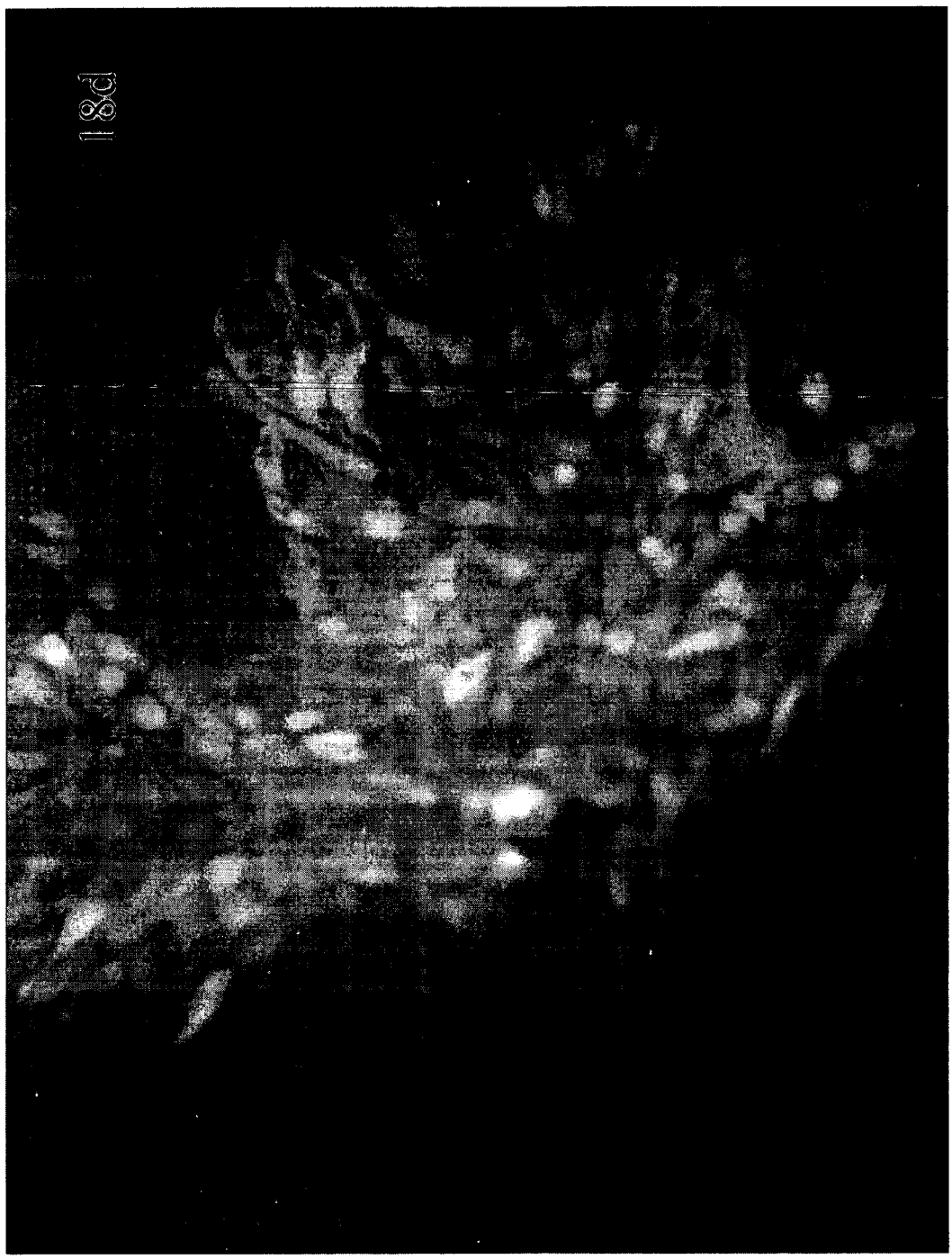
FIG. 9 illustrates a fluorescent micrograph of a large, potentially stable GFP+ colony 22 days after cellular integration with a plasmid spotted nanofiber array (scale bar=50 µm), representing an embodiment of the invention.

During these transfection experiments, reproducible GFP expression (GFP+) patterns were observed. For the chips that were pressed following centrifugation, GFP+ cells and clusters were observed both upon the chip and also in regions of the culture dish off the chip. These latter GFP+ cells had apparently received plasmid from fibers but had disassociated from fibers and reattached elsewhere in the culture dish during manipulations. Both on and off-chip, as a GFP+ cell divided, delivered plasmid would be segregated to progeny, which in turn would express GFP. GFP segregation could thus be observed with the formation of GFP+ cell clusters and often, these clusters would result in large, potentially stable, colonies of GFP+ cells. Such a colony is shown in FIG. 9. This colony resulted from the merging of three separate clusters of GFP+ cells on a chip that only had 20 initial GFP+ cells at 24 hrs following the fiber/cell integration. It is important to note that there is high probability that plasmid DNA is often delivered directly to the nuclear domain as the nuclear target can be a substantial fraction of the cell's overall projected area. In addition to providing a large dose of plasmid DNA to the nucleus, direct nuclear delivery may also shield the plasmid from cytosolic degradatory pathways that limit many other transfection methodologies. This nuclear delivery mechanism may explain the relatively high probability of colony formation, such as demonstrated by the colony shown in FIG. 9.

In contrast to these results, an intriguing observation was that, occasionally, a GFP+ cell on the chip did not generate any GFP expressing progeny, even over relatively long time periods (22 days). In these cases, it appeared plasmids were being retained by the original GFP+ cell, but were not being segregated to progeny cells. This behavior may be due to fiber delivery of plasmid DNA directly into the nuclear domain, but without release of the plasmid from the fiber for subsequent partitioning into progeny. Rather, plasmids might be immobilized to the fibers due to multiple electrostatic interactions. While tightly held, regions of these plasmids may still be accessible for transcriptional activity. In the plasmid used in these experiments, the active mammalian coding regions are only about 30% of the overall plasmid length. Thus, tethered plasmids may be held such that the GFP site was still available for polymerase binding and transcription.

To test this model, the inventors prepared VACNF chips with plasmid DNA covalently linked to the fibers such that there could be no segregation of plasmid to progeny. VACNF control chips were also prepared identically to the covalent chips—but without the linking agent during incubation. Both sets were extensively rinsed following the incubation step to remove non-specifically adsorbed plasmid. The inventors conducted a VACNF-mediated transfection experiment using four chips with plasmids covalently bound to the VACNFs and four control chips. The bound samples resulted in 81, 198, 65, and 102 GFP+ cells on each chip, respectively. The control samples resulted in no transfected cells on three chips and one faint GFP+ cell on the fourth, indicating that non-specifically adsorbed plasmid DNA had effectively been removed from the samples during rinse steps. Unlike previous experiments with spotted samples, no off-chip GFP+ cells were observed with the covalently-bound chips—providing evidence that GFP expression required the continued integration of cells with fibers.

FIG. 10A illustrates the dramatic differences in GFP expression from cells integrated with VACNFs with either spotted (top) or covalently linked (bottom) DNA. The spotted sample produced colonies of GFP+ cells from initial transfectants while the covalent sample maintained a nearly constant number of GFP+ cells over a 22 day period (days 6 and 14 shown). While growth and proliferation is occurring on both types of chip, the bound plasmid is not available for segregation on the covalently-derivitized chip. Thus, only the originally integrated mother cell (which remains integrated with the plasmid-derivitized fiber) remains GFP+. FIG. 10B follows a typical GFP+ cell on a covalently derivitized chip. Between day 7 and 8, this cell divided. Following this division, the mother cell continues to indicate GFP fluorescence while the GFP intensity decreases and ultimately ceases in the progeny cell. The daughter cell is still seen in bright field optical images (FIG. 10c), but it did not receive the tethered GFP plasmid during mitosis and is therefore not producing GFP.

The inventors have observed long-term expression of GFP (weeks) within cells with an incorporated VACNF and have achieved this expression on a parallel basis with many cells. This indicates that the integration of carbon nanofiber arrays with live cellular matrices provides realization of an intracellular biochemical interface for relatively long term applications, such as biosensors, protein factories, and in-vivo diagnostic tools. As the carbon nanofiber may be integrated as an active element into a wide array of electrical and electrochemical devices, the inventors believe this provides a basis for a much broader range of devices engineered to interface directly to cellular matrices. Ultimately, this parallel integration may provide a new toolset for interrogation and control of subcellular phenomena.

Cell Culture and Handling

The cell lines used predominantly for these experiments were a subclone of the Chinese hamster ovary cell line (CHO), designated $K_1$—$BH_4$ and kindly provided to us by Dr. A. W. Hsie. Additionally, an adherent mouse monocyte cell line, J774a.1, and Jurkat, a human lymphocyte line grown in suspension culture were also used. The characteristics and uses of CHO $K_1$—$BH_4$ have been extensively described by Hsie and co-workers [23]. CHO cells were routinely grown in Ham's F-12 nutrient mixture (Cat.#11765-054, GibcoBRL, Gaithersburg, Md.) supplemented with 5% fetal bovine serum (qualified, heat-inactivated, Cat.#16140-071, Gibco-BRL) and 1 mM glutamine (Cat.#G-6392, Sigma Chemical Co., St Louis, Mo.). J774a.1 was cultured in Dulbecco's Modified Eagle Media (DMEM), supplemented with 10% FBS and 2 mM glutamine. Jurkats were cultured in RPMI 1640 supplemented with 10% FBS. Cell cultures were grown in T-75 Flasks (Falcon #3111, Becton Dickinson & Co, Franklin Lakes, N.J.) and passaged at 80% confluency by trypsinization using trypsin-EDTA (Cat.#15305-014, Gibco-BRL) for CHO and scraping for J774a.1. Cells were counted using a Coulter Counter, Model Z1 (Coulter Corp, Hialeah, Fla.).

In preparation for fiber-mediated plasmid delivery, adherent cells were trypsinized or scraped from T-75 flasks, pelleted at 100 G for 10 min, resuspended in phosphate buffered saline (PBS), counted, and diluted in PBS to a density of 400,000-600,000 cells/ml. While not crucial to successful integration of fibers with cells, washing cells of serum containing media prior to integration protects the cells from the potential affects of direct administration of serum into the intracellular domain.

Fiber Synthesis

A pattern of 0.5 µm diameter dots with 5 µm space in between was produced by photolithography on standard 100 mm silicon wafers. A Ti buffer layer (100 Å) and Ni catalyst layer (1600 Å) were deposited using physical vapor deposition. The metal was then removed by dissolving photoresist in acetone leaving metallization only on dots. Vertically aligned carbon nanofibers were grown by direct current plasma enhanced chemical vapor deposition. A mixture of $C_2H_2$ and $NH_3$ gases were introduced into a chamber at flow of 50 sccm and 80 sccm respectively and 3 Torr of total pressure. The wafer was kept at 700 C during growth. The plasma current was 300 mA and voltage was 450 V. The growth was stopped after 50 min that resulted in 6 µm long VACNFs.

Microcentrifuge Spin Tubes

In initial studies of CHO pelleting onto nanofiber arrays, centrifugation was performed using typical mammalian pelleting parameters (50-100 G, 10 minutes) in a swinging bucket centrifuge. This centrifuge was limited by its construction to relatively low velocities (<2500 RPM) and long spin-up times (minutes). To streamline experiments, a modified eppendorf tube was developed for implementation with a microcentrifuge. As microcentrifuge rotors typically employ a rotor that holds tubes at a 45 degree angle, the modified eppendorf tube was designed to feature a 45 degree slanted surface such that a small (~5 mm×5 mm) fibered chip specimen could be positioned on the slant normal to centrifugal force. Eppendorf tubes (Safe Lock 1.5 mL, Cat #2236320-4, Brinkmann Instruments, Westbury N.Y.) were filled with approximately 750 µL of a 10:1 preparation of a two-component, polydimethylsiloxane (PDMS) reagent system (Sylgard 184, Dow Corning, Midland, Mich.) and cured overnight at room temperature while spinning at 6000 RPM in a microcentrifuge. This preparation provided a rigid, optically transparent, non-reactive, slanted base within the eppendorf tube, upon which fibered chips could be placed and retained such that their fibers were oriented parallel to the centrifugal force imposed on cells during microcentrifugation. Modified tubes were sterilized in an autoclave prior to use.

Spotting of Nanofiber Arrays with Plasmid DNA

Fiber arrays were spotted with plasmid DNA at various dilutions using a 2.5 µL pipettor. A 1 µL spot would wet a region of the chip approximately 1 mm in diameter. Following spotting, the fibered chips were air-dried in a sterile culture hood and then placed fiber-side up upon the PDMS slant of the modified eppendorf tubes. Plasmids employed were pGreen Lantern-1 (previously available as Cat #10642-015, Gibco BRL, Gaithersburg, Md.) which contains an enhanced green fluorescent protein (eGFP) gene with CMV immediate early enhancer/promoter and SV40 t-intron and polyadenylation signal; and constructs of the pIRES-EGFP and pIRES-EYFP plasmids (BD Biosciences Clontech, Cat #6032-1, Palo Alto, Calif.). Plasmids were routinely propagated in DH5-α E. coli selected with 50 µg/mL ampicillin. Plasmids were harvested using a commercially available purification system (Wizard® PureFection Plasmid DNA Purification System, cat #A2160, Promega, Madison, Wis.).

Emancipation of Catalyst Particle at Nanofiber Tips

Fiber arrays were exposed to a 5 min RF oxygen plasma etch process (RF power=250 watts, pressure=350 torr, oxygen flowrate=50 sccm). Following this treatment, fiber arrays were inspected with scanning electron microscopy in upper and lower detector modes to evaluate the presence of nickel catalyst and the removal of graphitic-C film on the catalyst surface. To further verify catalyst emancipation from the graphitic-C film, non-etched and oxygen-etched fibers were soaked in a dilute solution of 50 nm diameter latex beads (Polysciences Inc, Warrington, Pa.) and SEM imaged after drying the sample. The oxygen-etched fibers tended to collect latex beads at the tips of fibers where catalyst was exposed, presumably due to electrostatic interactions between the negatively charged latex beads and exposed nickel.

Covalent Modification of Fibers with Plasmid DNA

Similar to catalyst emancipation, fiber arrays were exposed to a 5 min RF oxygen plasma etch process. This provided oxygen-containing moeities, including carboxylic acid groups, on the fiber surface, including the carbon-rich region at fiber tips. Small portions of fibered substrates (~3×3 mm square) were placed in an eppendorf tube and covered with 1 ml of 0.1M MES (2-[N-morpholino]ethane sulfonic acid at a pH of 4.5) buffer containing 10 mg of EDC (1-ethyl-3-(3-dimethylaminopropyl)carbodiimide) and 1 µg of plasmid DNA. This reaction mixture was agitated on an orbital shaker for two hours at room temperature. The samples were then rinsed in two 1 ml aliquots of phosphate buffered saline and soaked in 1 ml of PBS for 1 hour at 37 deg C. The samples were then rinsed in deionized water and soaked for 1 hour in water at 37 deg C. In parallel, control samples were prepared identically except for containing no EDC during the initial incubation step. Integration of cells with the EDC prepared fiber/plasmid arrays resulted in transfection efficiencies from 1-30% (dependent upon volume of MES buffer employed). Integration of cells with fibers that had been incubated with plasmid in MES buffer without EDC in solution resulted in effectively 0% transfection—indicating that non-specifically adsorbed DNA is effectively removed from fibers during rinse steps following the EDC condensation reaction.

Centrifugation of Cells onto Carbon Nanofiber Arrays

Figure 11A:
FIGS. 11A-11D illustrate scanning electron micrographs of cells following (FIG. 11A) centrifugation, (FIG. 11B) press, and (FIGS. 11C and 11D) culture for 48 hours prior to SEM imaging (scale bars=10 µm), representing an embodiment of the invention.
Figure 11B:
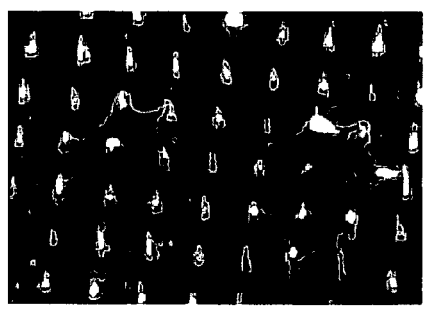
Figure 11C:
Figure 11D:
Figure 12A:
FIGS. 12A-12B illustrates laboratory results, representing an embodiment of the invention.
Figure 12B:

500 µL of CHO cells at a density of 100,000-600,000 cells/ml were placed in the modified eppendorf tube. Tubes were placed within a microcentrifuge such that the PDMS slanted surface was oriented normal to the centrifugal force, and thus fibers were oriented parallel to the pelleting force of centrifuged cells. Referring to FIG. 11A, cells were spun down upon the fibered substrates at 600×G for 30 s to 1 min. Optionally, referring to FIG. 11B, following the spin, the substrate was inverted and pressed against a flat, wetted surface to further integrate the spun cells with the fiber matrix. Following the spin and press, the fibered substrates were transferred into either 35 mm culture dishes with 1.5-2 mL of media or into individual wells of 24-well plates containing 1 mL of media per well. Cells were incubated for at least 24 hours prior to SEM imaging (FIG. 11C-11D) or fluorescent microscopy for evaluation of fluorescent protein expression (FIGS. 12A-12B).

EXAMPLES

Specific embodiments of the invention will now be further described by the following, nonlimiting examples which will serve to illustrate in some detail various features. The following examples are included to facilitate an understanding of ways in which the invention may be practiced. It should be appreciated that the examples which follow represent embodiments discovered to function well in the practice of the invention, and thus can be considered to constitute preferred modes for the practice of the invention. However, it should be appreciated that many changes can be made in the exemplary embodiments which are disclosed while still obtaining like or similar result without departing from the spirit and scope of the invention. Accordingly, the examples should not be construed as limiting the scope of the invention.

First Set of Examples

A first set of examples of the invention include intracellular integration of synthetic nanostructures with viable cells for controlled biochemical manipulation. This example demonstrates the integration of vertically aligned carbon nanofiber (VACNF) elements with the intracellular domains of viable cells and controlled biochemical manipulation of cells using the nanofiber interface. Deterministically synthesized VACNFs were modified with either adsorbed or covalently-linked plasmid DNA and were subsequently inserted into cells. Post insertion viability of the cells was demonstrated by continued proliferation of the interfaced cells and long-term (>22 day) expression of the introduced plasmid. Adsorbed plasmids were typically desorbed in the intracellular domain and segregated to progeny cells. Covalently bound plasmids remained tethered to nanofibers and were expressed in interfaced cells but were not partitioned into progeny, and gene expression ceased when the nanofiber was no longer retained. This provides a method for achieving a genetic modification that is non-inheritable and whose extent in time can be directly and precisely controlled. These results demonstrate the potential of VACNF arrays as an intracellular interface for monitoring and controlling subcellular and molecular phenomena within viable cells for applications including biosensors, in-vivo diagnostics, and in-vivo logic devices.

An emerging goal of postgenomic research is the development of an understanding of gene circuit and network structure and function that give rise to complex cell functionality. To date, work in this direction has been focused on the analysis, modelling, and simulation of gene circuits [1] or the development of synthetic gene circuits which mimic electronic functionality [2] such as a toggle switch [3], an oscillator [4], or combinatorial logic gates [5,6]. While these software and 'cellware' elements provide invaluable tools for the exploration of gene circuit and network structure and function, the missing elements are hardware tools that close the feedback loop between simulation and experiment. Such tools are considered indispensable in the analogous field of electronic device modelling, and are likely to play a similar role in genetic circuit modelling and design. The ideal tools would interface directly with the appropriate biomolecular processes, allow the introduction of stimuli, and provide transduction of responses with both spatial and temporal resolution, all performed without adversely affecting cell viability or functionality.

Engineered nanoscale devices may provide realization of tools for monitoring and manipulating cellular processes, as they reside at the same size scale as the biomolecular machines of cells. Such an interface of nanotechnology and biotechnology has been demonstrated by using non-bleaching fluorescent nanocrystals in place of dyes for monitoring cellular processes [7-9]. Pulled glass capillaries with nanoscale tips have also been implemented for cellular and subcellular electrophysiological monitoring [10] and for biochemical manipulation of cells via microinjection of membrane-impermeable molecules (e.g. proteins, DNA) [11]. While these nanoscale interfaces have dramatically increased our knowledge of cellular processes, they conventionally are limited to techniques that require manipulating cells one at a time using individual elements observed under a microscope, and thus typically provide only a serial interface to cells. Parallel embodiments of these devices have been fabricated using silicon microfabrication methods [12], but, as with all micromachining techniques, there are limitations to the ultimate size scale and density of features (tip radii and spacing of the silicon needles) and a limited choice of substrate materials which are often not well-suited for cell culture or observation due to material incomparability or optical opacity.

Carbon nanotubes (CNTs) and related nanostructures provide a new approach to nano- and microdevice fabrication that avoid many of the limitations of micromachining while providing the means to construct addressable, functional nanoscale devices including chemically specific AFM probes [13,14] electrochemical probes [15], and electromechanical manipulators [16]. Within this family of structures, carbon nanofibers are uniquely suited for the construction of intracellular devices because of the ability to exquisitely control their synthesis. Deterministic arrays of closely-spaced (pitch ≥1 µm) vertically aligned carbon nanofibers (VACNFs) [17-19] may be grown on a wide variety of substrates (including quartz and glass slides) with wide bases that provide mechanical strength while still generating a small diameter tip (≥5 nm tip radius) appropriate for insertion directly into cells. The inventors show a critical enabling step toward the hardware tools needed for the coupling of gene circuit simulation with experiment by demonstrating the functional, parallel integration of VACNF elements within cells. The viability of the cells after VACNF insertion is demonstrated by the long-term expression of a constitutively-expressed green fluorescent protein (GFP) gene carried on nanofiber-borne plasmid molecules. This hybrid combination of cell and nanostructure accomplished gene expression from plasmid DNA both adsorbed and tethered to the VACNFs, where tethered plasmid molecules were not partitioned into progeny after cell division. This provides a method for achieving a genetic modification that is non-inheritable and whose extent in time can be directly and precisely controlled. In addition to gene circuit characterization, this capability may address other more general genetic manipulation needs such as controlling the time course of gene expression during critical cell or embryo development [20].

Materials and Methods

Vertically-aligned nanofiber arrays were synthesized from 500 nm diameter nickel catalyst dots that were photolithographically defined at 5 µm intervals on 100 mm, n-type silicon wafers. VACNF growth was accomplished using a previously described plasma-enhanced chemical vapor deposition process [18,19]. In brief, the wafer was maintained at a temperature of 700 deg C., while a mixture of $C_2H_2$ and $NH_3$ was introduced into a PECVD chamber at 3 Torr of total pressure. Plasma was initiated and maintained at 450 V and 300 mA. Growth of individual fibers resulted from catalytic deposition of carbonaceous material through the nickel particle at the growing-fiber tip, and deposition of carbonaceous material on the fiber surface. The ammonia served as an etchant to remove a passivating carbon film that continuously forms on the surface of the catalyst particle, and also as a source of nitrogen doping for the growing structure. Typical growth resulted in conically-shaped fibers of 6-10 µm length (depending upon growth time) with tip diameters of 20-50 nm and base diameters of approximately 1 µm. Following nanofiber growth, the wafers were cleaved into 3 mm×3 mm chips that were covered with VACNF arrays with a 5-µm pitch (FIG. 8). FIGS. 8 and 7A-7C illustrate structures and process used for the integration and biochemical modification of cells.

Following synthesis, nanofiber arrays were surface-modified with plasmid DNA. The plasmid used in these experiments was pGreenLantern-1 (previously available as Cat #10642-015, Gibco BRL, Gaithersburg, Md.) which contains an enhanced green fluorescent protein (eGFP) gene with the CMV immediate early enhancer/promoter and SV40 t-intron and polyadenylation signal. This plasmid contains no mammalian origin of replication, therefore serving as a reporter system for transient expression in eukaryotic cells. Plasmid DNA at various concentrations (5-500 ng/µl) was either spotted onto the chips as 0.5-1 µl aliquots and allowed to dry or covalently tethered to the nanofibers. For covalent attachment, VACNF arrays were etched for 5 min in an RF oxygen plasma to provide oxygen-containing moieties, including carboxylic acid groups, on the nanofiber surface. The chips were then covered with 1 ml of 0.1M MES buffer (2-[N-morpholino]ethane sulfonic acid at a pH of 4.5) containing 10 mg of EDC (1-ethyl-3-(3-dimethylaminopropyl)carbodiimide) and 1 µg of plasmid DNA. This reaction mixture was agitated on an orbital shaker for two hours at room temperature to condense primary amines on DNA to the carboxylic acid sites of oxygen plasma etched fibers [21,22]. In parallel, control samples were prepared identically except no EDC was used during the incubation step. Both sample types were then rinsed extensively in phosphate buffered saline and water to remove non-specifically adsorbed DNA.

The cell line used predominantly for these experiments was a subclone of the Chinese hamster ovary (CHO) designated $K_1$—$BH_4$ and provided to us by Dr. A. W. Hsie [23]. Cells were routinely grown in Ham's F-12 nutrient mixture (Cat.#11765-054, GibcoBRL, Gaithersburg, Md.) supplemented with 5% fetal bovine serum (qualified, heat-inactivated, Cat.#16140-071, GibcoBRL) and 1 mM glutamine (Cat.#G-6392, Sigma Chemical Co., St Louis, Mo.). Cell cultures were grown in T-75 Flasks (Falcon #3111, Becton Dickinson & Co, Franklin Lakes, N.J.) and passaged at 80% confluency by trypsinization using trypsin-EDTA (Cat #15305-014, GibcoBRL). In preparation for fiber-mediated plasmid delivery, adherent cells were trypsinized from T-75 flasks, quenched with 10 ml of Ham's F12 media, pelleted at 100 G for 10 min, resuspended in phosphate buffered saline (PBS), counted, and diluted in PBS to a desired density ranging from 50,000 to 600,000 cells/ml.

To interface cells to DNA modified nanofiber arrays, CHO cells were centrifuged at 600 G out of suspension in PBS onto these chips, which resulted in some cellular impalement on VACNFs (FIG. 7A). Optionally, to increase the probability and depth of fiber penetration into cells, the chip was then gently pressed against a flat, wetted surface following the spin (FIG. 7B). Following these integration steps, the chip was placed in growth media in a culture dish and incubated to allow cell recovery and proliferation (FIG. 7C).

Results and Discussion

In these experiments, The inventors employed the expression of a reporter gene, GFP, to indicate successful intracellular integration and delivery of plasmid DNA by the fiber and to provide a marker for continued viability of the interfaced cell. For this approach to work, the nanofiber array must retain DNA during cellular manipulations, penetrate the membrane boundary of cells, and deliver DNA to the intracellular domain. Finally, the delivered plasmid DNA must also be expressed within the recipient/interfaced cells.

CHO cells are approximately 7 μm diameter spheres while in suspension. As such, nanofiber arrays were synthesized at a pitch of 5 μm, such that, during centrifugation and the optional press step, a cell would likely interact directly with only a few nanofibers. Typical results of these interactions are shown in FIGS. 11A-11C. Immediately following centrifugation, cells retained their rounded shape and were loosely coupled with the chip (FIG. 11A). When the press step was used, the cells tended to deform from their spherical shape and attach to the nanofibers and interfiber surfaces of the substrate (FIG. 11B). In either case, the cells eventually began to attach and stretch out on the substrate and continue to proliferate (FIG. 11C).

Following a culture period of at least 24 hours, the interaction of plasmid-spotted nanofibers and cells was evaluated by observing plasmid-coded GFP expression with fluorescence microscopy. When cells were centrifuged onto the array at 600 G, GFP expression (GFP+) was detected in cells at only a very low frequency (<1% of the cells on the fibered substrate). Pelleting forces were increased to as high as 5000 G with no apparent increase in GFP+. Increasing the pelleting forces further resulted in significant cell death and the inability of surviving cells to recover from the pelleting process. Using a moderate pelleting force (600 G) to position cells upon the nanofiber array, and then including a subsequent press step (FIG. 11B) typically increased the number of GFP+ cells, often by as much as a factor of 5 and occasionally even more significantly, with some tests resulting in ~50% of cells in local regions of the substrate (~1 mm$^2$ areas) being GFP+. While the press step introduced much variability in the yield of GFP+ cells, it appeared necessary in order to cause fiber penetration (and DNA delivery) into the intracellular domain.

An important factor influencing the amount of GFP+ observed following these integration steps was nanofiber composition. In general, nanofibers comprised exclusively of carbon resulted in extremely low yields of GFP+ cells (<<1%)—even using the press step to increase fiber penetration. This low yield appears to not be indicative of low probability of fiber penetration into cells, but rather due to low retention of DNA on these structures and loss of plasmid prior to cell/fiber interaction. In fluorescent tagging and gel-electrophoresis-based studies of plasmid adsorption and desorption from VACNFs, carbon-rich VACNFs did not retain DNA during even gentle rinsing (data not shown). The surface chemistry of nanofibers, however, may be altered during synthesis to feature high levels of nitrogen content, ranging from essentially 0 to more than 50 atomic % as measured by energy dispersive x-ray spectroscopy [24]. In contrast to the poor DNA retention of exclusively carbon nanofibers, nitrogen-containing VACNFs retained more DNA during rinsing, presumably due to electrostatic interactions between the anionic phosphate backbone of the DNA and the nitrogen-bearing sites on the nanofibers. It is with nitrogen-bearing nanofiber arrays that the relatively high-yields of GFP+ were observed.

Using nitrogen-bearing nanofibers that had been spotted with plasmid DNA, reproducible GFP expression patterns were observed following cell recovery and proliferation. For the chips that were pressed following centrifugation, GFP+ cells and clusters were observed both on the chip and also in regions of the culture dish off the chip. These latter GFP+ cells had apparently received plasmid from VACNFs but had disassociated from the chip and reattached elsewhere in the culture dish during manipulations. Both on and off-chip, as a GFP+ cell divided, delivered plasmid would be segregated to progeny, which in turn would express GFP. Plasmid segregation was observed with the formation of GFP+ cell clusters, and often these clusters would result in large, potentially stable colonies of GFP+ cells, as shown in FIG. 9. This colony resulted from the merging of three separate clusters of GFP+ cells on a chip that was intentionally integrated with only a sparse layer of cells, and which only had 20 initial GFP+ cells 24 hrs after being placed on the chip. In the same experiment, another chip with only 8 initial GFP+ cells also generated a large, potentially stable GFP+ colony. These relatively high probabilities for potentially stable colony formation may be due to plasmid DNA being delivered by nanofibers directly to the nuclear domain. In CHO cells, the nuclear target (2-3 μm diameter) is a substantial fraction of the cell's overall projected area (7 μm diameter). Thus, nuclear impalement may frequently coincide with cellular impalement by the nanofibers.

In contrast to these results, an intriguing observation was that occasionally a GFP+ cell on the chip did not generate any GFP expressing progeny, even over relatively long time periods (22 days). In these cases, it appeared plasmids were being retained and expressed by the original GFP+cell, but were not being segregated to progeny cells. The inventors postulated that this behavior was due to VACNF penetration directly into the nuclear domain but without release of the plasmid from the VACNF. If the plasmid is immobilized to a nanofiber, it is not free to segregate into progeny cells. Further, as this plasmid does not contain a mammalian origin of replication (ORI), immobilized plasmids could not be used as templates to generate additional, free copies of the plasmid. Plasmid molecules may have been immobilized on the nanofibers due to multiple electrostatic interactions [25] at portions of their circular structure while other, active coding regions of these same plasmids remained unbound and accessible for transcriptional activity. For the plasmid used in these experiments, the active mammalian coding regions are only about 30% of the overall plasmid length. Thus, with potentially large numbers of plasmids on each nanofiber, it is likely that some plasmid molecules were immobilized such that the entire GFP site was still available for polymerase access and transcription.

To test this model the inventors prepared VACNF chips with plasmid DNA covalently linked to the VACNFs such that there would be minimal free plasmid available for segregation to progeny. The inventors conducted a centrifugation and press integration method using four chips with plasmids covalently bound to the VACNFs using an EDC-condensation reaction and four control chips that had been incubated with the DNA reaction mixture, but without the EDC. Both sample types were extensively rinsed following the incubation step. For the control samples, without EDC in the reaction mix, there should be no covalent binding of DNA to the nanofiber scaffold and subsequent extensive rinsing would remove non-specifically bound DNA from the nanofibers. Following centrifugation and pressing of cells onto these fibered chips, the covalently-linked samples resulted in 81, 198, 65, and 102 GFP+ cells on each chip, respectively. The control samples resulted in no GFP+ cells on three chips and one faint GFP+ cell on the fourth, indicating that non-specifically adsorbed plasmid DNA had effectively been removed from the samples during rinse steps. Unlike previous experiments with samples non-covalently spotted with plasmid, no off-chip GFP+ cells were observed, indicating that GFP expression required the continued retention of the DNA-derivitized VACNF element within the cell.

FIG. 10A illustrates the dramatic differences in GFP expression from cells integrated with VACNFs with either spotted (top) or covalently-linked DNA (bottom). The spotted sample produced colonies of GFP+ cells from initial transfectants while the covalently linked sample maintained a nearly constant number of GFP+ cells over a 22 day period (days 7 and 14 shown). While growth and proliferation is occurring in both cases, the covalently bound plasmid is not available for segregation to progeny, and only the cells that retain a plasmid-derivatized nanofiber remain GFP+. FIG. 10B follows a typical cell on a covalently linked chip. Between day 7 and 8, this cell divided, and the mother cell (denoted '1') continued to fluoresce for several days, indicating the continued expression of GFP. Fluorescence continued in the progeny cell (denoted '2') for a short period following division, presumably due to partitioning of the GFP protein. However, this fluorescence decreased and ultimately ceased within approximately one day, indicating the decay of the partitioned protein and the absence of new GFP synthesis. The GFP-daughter cell was still present on the chip as seen in bright field optical images (FIG. 10C).

The inventors have shown that arrays of carbon nanofiber elements may be functionally integrated within cells which remain viable after VACNF insertion. This successful integration provides an intracellular biochemical interface that is a critical enabling step in the realization of hardware tools that couple modelling and experiment in genetic circuit and network exploration and design. While the functioning of this hybrid combination of cell and synthetic nanostructure was demonstrated by observing long-term gene expression from nanofiber-bound plasmid molecules, it demonstrates that other functional properties of VACNFs may be used during intracellular deployment without compromising cell viability. For example, previously demonstrated VACNF electrochemical probes [15] could be deployed within cells, or electronically or heat activated methods [26] for binding or releasing the active coding regions of the delivered plasmid to the nanofiber could provide very specific temporal control of gene expression. Additionally, in our experiments there was evidence of a high incidence of nuclear delivery of plasmid using VACNF vectors. If so, this would overcome a lack of nuclear targeting and may shield delivered DNA from cytosolic degradative pathways, each of which are frequently cited as a limitation of transfection methods [27]. Application of both intracellular control elements and efficient DNA delivery go well beyond applications of gene circuit and network probing. For example, VACNF-mediated delivery may prove useful when other transfection methods are toxic to the cell [28], or where the expression of a delivered gene is needed for a limited but well controlled time period for the optimized development of a cell or embryo [20]. In any of these applications, the controlled synthesis and directed assembly of synthetic nanoscale structures provide the means to directly manipulate bimolecular processes in cells or to bridge the gap between informational pathways in living and synthetic systems. Advances in this coupling of nanotechnology and biotechnology hold the promise of providing flexible methods for genetically manipulating cells and providing deeper insights into the complex systems which give rise to cellular function.

Second Set of Examples

Examples of the invention include nanostructures for spatially-resolved macromolecular delivery to viable whole cells. This example evaluates a new interface for the spatially-resolved introduction of macromolecules into plant, animal, and bacterial cells/tissue is proposed. This methodology can include the fabrication of vertically-aligned carbon nanofiber arrays to provide needlelike molecular-scale structures well-suited for mechanical delivery of macromolecules through the walls and membranes of cell cultures and tissue. Arrays of solid, needlelike features comprised of high aspect ratio, vertically-aligned carbon nanofibers can be grown on porous substrates. The porous substrate enables flowthrough deposition of macromolecules at discrete regions of nanofiber arrays. The nanofiber arrays can be employed to mechanically impale targeted cells, in turn loading these cells with the deposited material. The ability to spot CNF structures with arrays of macromolecules and to use these structures for cellular loading of molecules and molecular combinations at known spatial intervals, provides a powerful new combinatorial tool for genetic and pharmaceutical research.

The invention can directly support laboratory missions in nanotechnology and complex biological systems, and can include nanostructure growth and derivitization in combination with cellular and genomic manipulation. The invention can include optimizing carbon nanofiber growth on porous substrates, derivitization and evaluation of biomolecular interactions with carbon fiber surfaces, development of flowthrough material spotting methods, evaluation of the interaction of the carbon nanoscale interface with cells and tissue, and evaluation of the efficacy of these systems for material delivery into targeted cells and tissue.

The carbon nanofiber provides a unique new approach to microinjection- and whisker-mediated material delivery to cells. They feature extremely large length to diameter (aspect) ratios, but provide tip diameters 2 to 3 orders of magnitude smaller (20 nm vs 1 micron). This diameter reduction ($1/500^{th}$ the diameter of a typical mammalian cell) makes carbon nanofibers extremely well-suited for material delivery to individual cells—introducing new material while minimizing the trauma of cellular penetration. Additionally, carbon fibers are synthesized in highly ordered arrays with each needlelike element growing perpendicular to the substrate, thereby providing an ideal format for parallel nanoinjection strategies. The inventors have pioneered the controlled growth of these structures in a variety of geometrical formats [18-19, 24, 29] on a variety of conducting and insulating substrates (silicon, quartz, tungsten), within holes and fluidic channels, and even demonstrating electrical addressing of individual nanofiber elements [15]

As noted above, the invention can include the fabrication of nanofiber needle arrays on porous, flowthrough substrates. The nanofiber elements will provide molecular-scale features that may be coated with macromolecules for delivery into intact cell layers and tissue. The porous substrates will enable improved hydrodynamic approach of the fibers to cells and tissue while providing highly resolved material spotting at discrete locations on the nanofiber arrays. The invention can provide an interface for patterned material delivery to regions of tissue and cell cultures. The entire structure (with overall substrate dimensions up to several 10 s of square centimeters) can be implemented simply by pressing the fibered substrate into cell cultures and tissue. The resulting patterned material delivery will provide a powerful new tool for genomic and pharmaceutical exploration in an easy to use (and ultimately inexpensive to fabricate) format.

Figure 13:
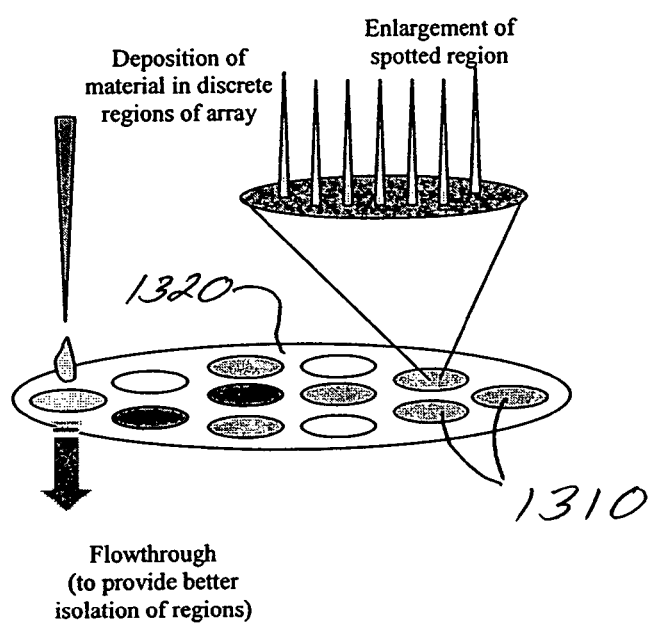
FIG. 13 illustrates fibered material delivery arrays, representing an embodiment of the invention.

FIG. 13 illustrates fibered material delivery arrays 1310 fabricated to enable pattered material delivery to cells and tissue. Twelve arrays 1310 are configured on a porous substrate 1320.

Figure 14:
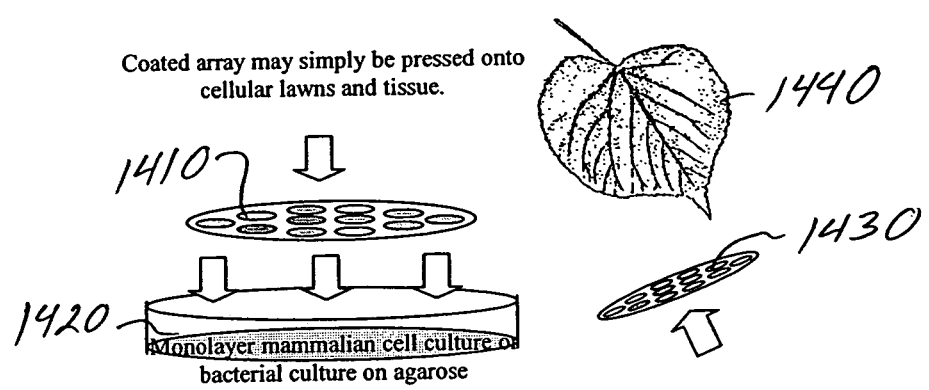
FIG. 14 illustrates an implementation of fibered material delivery arrays, representing an embodiment of the invention.

FIG. 14 illustrates an implementation of fibered material delivery arrays may be as simple as pressing arrays into targeted cell cultures and/or tissue, resulting in patterned material delivery to isolated regions of tissue. A first array 1410 is shown being lowered into a culture 1420. A second array 1430 is shown being moved toward a botanical sample 1440. The strength of the carbon fiber matrix may even provide material delivery to the cells of plant tissue, such as the underside of leaves.

The invention can include carbon fiber growth on porous substrates. The invention can align fiber growth on porous materials to provide a flowthrough substrate for subsequent material deposition. A flowthrough substrate is desirable to this effort as it minimizes diffusive and capillary transport of the spotted material into adjacent regions of the fibered array and therefore provides for patterned deposition of different materials at discrete locations. The flowthrough substrate also provides for improved fluidic approach of the patterned array to a lawn of cells in an aqueous culture environment by enabling the aqueous cellular media to pass through the substrate rather than having to be pushed radially outward between the substrate and cells.

Figure 15:
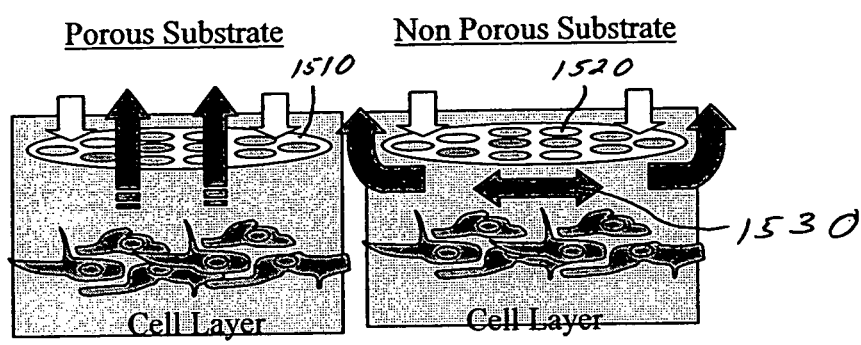
FIG. 15 illustrates that a porous substrate is desirable as it reduces the shear stress imparted to cells by displaced culture media during use, representing an embodiment of the invention.

FIG. 15 illustrates that a porous substrate 1510 is desirable as it reduces the shear stress imparted to cells by displaced culture media during use. A nonporous substrate 1520 requires fluid 1530 to be driven parallel to the cellular monolayer. This is stressful to cells, and would promote radial dispersion of the plasmid patterning on the fiber arrays.

Aligned fiber growth can be performed by catalyst assisted chemical vapor deposition of carbon from carbonaceous gases in a high temperature (600-750° C.) DC plasma. As such, the porous substrate material must be capable of withstanding these temperatures for extended periods. The invention can include growth of fibers on ceramic and metal filter materials upon which thin layers of catalytic material (Fe, Co, or Ni) have been deposited. To promote bonding of fibers with the substrate material, intermediate 'buffer' layers of metallization, between the catalyst sites and the substrate, may be advantageous. In addition to promoting adherence of fibers, these buffer metallization layers also provide for nanosized droplet formation from continuous films of the catalyst. This is accomplished using a high temperature pre-growth step during which the catalyst layer transitions from a solid to a liquid and breaks up into small, noncontiguous droplets. The size and dispersion of these droplets largely determines the ultimate tip radius and spacing between carbon fibers.

The invention can provide fibers with ~20 nm tip radius and interfiber spacings of a few microns. This spacing will provide several needlelike structures per cell for subsequent material delivery studies.

The invention can include derivitization and evaluation of biomolecular interactions with carbon fiber surfaces. The invention can include absorption and desorption of macromolecules on/from the needlelike nanostructures. In a preferred embodiment, the invention can include material delivery from nanofibers that is a largely passive process in which adsorbed material will be shed into the intracellular environment following membrane penetration. However, the invention can also include strong adsorption of material so that patterned regions do not diffusively intermingle prior to interfacing the fiber array to cellular targets. Carbon nanofibers feature a highly hydrophobic surface of rolled graphene sheets, with occasional hydrophilic defect sites (predominantly carboxy and carbonyl groups). The invention can include the use of strongly adsorbed hydrophobic dye materials onto the carbon fiber surface. Embodiments of the invention can include derivitized carboxylic acid groups of fibers using condensation reactions with amine functionalized fluorophores. The invention can also include 'pi-stacking' of a variety of fluorophores linked to a pi-bonding pyrene.

The invention can include the use of dye-labeled proteins and DNA in physiological buffer solutions (PBS and HEPES), with DNA (and particularly plasmid vectors) being preferred embodiments. The invention can include the patterning of native carbon fiber arrays with known concentrations of labeled molecules and use fluorescence microscopy to observe the fluorescence intensity of patterned (and adjacent) regions prior to and following rinsing with physiological buffer solutions. The invention can include the use of a microscope environmental chamber to ramp temperature while observing dye release from coated regions, thus providing a first order evaluation of binding energy for different molecules. The invention can include molecule(s) that are useful for improving the native surface with respect to binding, retention and release. The invention can include the use of fibers that are derivitized to provide improved material handling capability. The invention can include coating methods in which the desired molecule(s) to be delivered is(are) suspended in low concentration gelatinous matrices (0.2% agarose). The invention can include the actual functional derivitization of fibers, such as using pyrene stacking molecules with a variety of functional groups to modify the surface for improved material retention (in the extracellular environment) and intracellular release. The invention can include tethering molecules to fibers using covalent bonds to the fibers (via carboxy and carbonyl defects) that are only cleaved when exposed to the intracellular environment (i.e. intracellular esterase activity).

Where binding and release of molecules is determined fluorescently, the possible retention of labeled molecules within the porous substrate may provide a substantial background artifact. For this reason, preferred embodiment of the invention can include the use of metallic substrates (vs ceramic or polymeric) as metal substrate may retain significantly lesser amounts of DNA and other biomolecular species.

The invention can include flowthrough material spotting methods. The invention can include the use of fluorescent microscopy to investigate material spotting methods to provide patterned material deposition on (and patterned delivery from) nanofiber arrays. The invention can include spatially discrete material spotting achieved simply by applying vacuum to one side of a fibered array on a porous substrate and micropipetting material (using an available array spotting instrument) onto and through the array. Flowthrough rates should be adjusted to optimize the deposition. The invention can include balancing minimizing diffusive and capillary fluid spread into adjacent regions of the array, while allowing adequate flowthrough times for sufficient material to adsorb onto fiber surfaces. The invention can include fluid carriers used for spotting that maximum wetting of the carbon surface while still enabling partitioning of the macromolecules from the fluid carrier onto the solid carbon fibers. For species that are normally negatively charged under physiological conditions (most fluorescent dyes and DNA), The invention can include altering pH conditions in order to minimize repulsion from the COO— defects of the carbon fiber. The invention can include (on metal substrates) the use of electrophoretically assisted material deposition onto carbon fibers by using the substrate and fibers as the cathode in an electrophoretic circuit. The invention can include the application of electric potentials to fibers through the substrate [15]. In this way, the invention can include electrophoretic assisted material deposition (and/or release).

The invention can include arrays patterned with fluorescent proteins and DNA that is physically pressed into cellular matrices. The invention can include fluorescence microscopy to evaluate the transfer of dye-labelled protein and DNA to the cellular and tissue targets by observing the intensity of fluorescence remaining in the cellular matrices following pressing and removal of the fibered arrays. The invention can include adherent monolayers of mammalian cells (CHO, MVLN or J774a.1), bacterial cultures on agarose (*P. fluorescens* and *E. coli*), undifferentiated plant calli on agarose, and plant tissue (for example, the underside of leaf tissue from arabidopsis).

The invention can be used with the more plastic behavior of the plant cell wall; electron microscopy can be used to evaluate the surface features of plant tissue following material transfer with a nanofiber delivery system. The invention can include utilization of the mechanical interaction that occurs at the fiber/cell wall interface to affect what proportion of fibers break off and remain in the cellular matrix, if penetrations remain in the cell wall following the delivery procedure and the distribution of hole size and shape remaining in the targeted tissue. Although the percentage of fibers shear off the substrate during manipulations can sometimes be an issue, fiber arrays with bacterial matrices tolerate these stresses quite well (FIG. 16).

Figure 16:
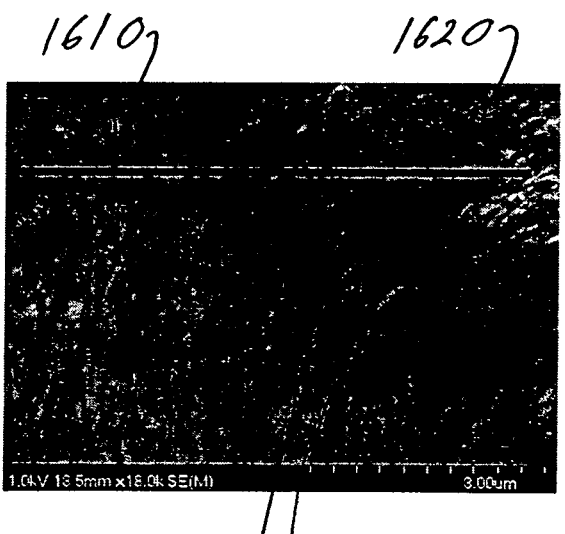
FIG. 16 illustrates an interaction between a native carbon fiber array and a bacterial matrix, representing an embodiment of the invention.

FIG. 16 illustrates the interaction between a native carbon fiber array 1610 and a bacterial matrix 1620 and indicates the robust mechanical strength of the fibers 1630. It should be noted how fibers 1630 are actually bent, without breaking, where they interface to the biomass. The solid black line indicates a typical size for a mammalian cell (7 μm).

Ultimately, effective material delivery is facilitated not only by material delivery from nanofibers into cells, but also the continued survival of these cells such that the consequences of material delivery may unfold. Cells will tolerate and survive the penetrations of the carbon nanofibers. The response of human fibroblast cell lines to penetrations with >1 μm diameter pulled capillaries has been documented [30]. While a significant 'wound response' of hydrogen peroxide exocytosis (presumably due to NADPH oxidase activity) results from these penetrations, the cells were able to recover. The invention can include the use of fiber tips that are almost 2 orders of magnitude smaller at the tip, and therefore should have significantly less impact upon cell physiology.

The invention can include the delivery of an unlabelled molecule into the cell interior and continued survival (and propagation) of that cell. An example is the patterning of nanofiber arrays with the Green Fluorescent Protein (GFP) plasmid (pGreen Lantern-1), which the inventors have previously used for genetic transformation of a variety of cell lines, including CHO, MVLN, and MCF7. Patterned arrays can be pressed into monolayer cultures of CHO, *P. fluorescens* (on agarose) and arabidopsis leaf tissue. These cultures can then be examined using fluorescence microscopy over a period of 7-14 days to observe if plasmid delivery occurred (expression of GFP within 72 hours), and whether transfected cells continue to survive and propagate.

Combinatorial techniques provide the ability to screen a large ensemble of synthesized molecules using an organized and deterministic methodology. As such, combinatorial synthesis is a significant research thrust in the exploration of pharmaceuticals. Similar approaches have incredible potential with respect to evaluating the impact of pharmacokinetic agents on actual cells and tissue. The ability to provide spatially indexed delivery of macromolecules to cells provides the basis for combinatorial evaluation of the functional effect of pharmacokinetic agents and genetic vectors.

Practical Applications of the Invention

The invention is useful in conjunction with biosensors, implantable cell and tissue diagnostics, cell culture research platforms, chemical/biochemical/electrophysiological research platforms, DNA delivery systems, pharmaceutical delivery systems, macromolecular delivery systems, parallel cellular probing, as well as parallel cellular manipulation and modification. The invention is useful in conjunction with protein factories. There are virtually innumerable uses for the invention, all of which need not be detailed here.

The invention can also be included in a kit. The kit can include some, or all, of the components that compose the invention. The kit can be an in-the-field retrofit kit to improve existing systems that are capable of incorporating the invention. The kit can include software, firmware and/or hardware for carrying out the invention. The kit can also contain instructions for practicing the invention. Unless otherwise specified, the components, software, firmware, hardware and/or instructions of the kit can be the same as those used in the invention.

The terms a or an, as used herein, are defined as one or more than one. The term plurality, as used herein, is defined as two or more than two. The term another, as used herein, is defined as at least a second or more. The terms comprising (comprises), including (includes) and/or having (has), as used herein, are defined as open language (i.e., requiring what is thereafter recited, but open for the inclusion of unspecified procedure(s), structure(s) and/or ingredient(s) even in major amounts. The phrases consisting of and/or composed of close the recited method, apparatus or composition to the inclusion of procedures, structure(s) and/or ingredient(s) other than those recited except for ancillaries, adjuncts and/or impurities ordinarily associated therewith. The recital of "essentially" along with "consisting of" or "composed of" renders the recited method, apparatus and/or composition open only for the inclusion of unspecified procedure(s), structure(s) and/or ingredient(s) which do not materially affect the basic novel characteristics of the composition. The term coupled, as used herein, is defined as connected, although not necessarily directly, and not necessarily mechanically. The term approximately, as used herein, is defined as at least close to a given value (e.g., preferably within 10% of, more preferably within 1% of, and most preferably within 0.1% of). The term substantially, as used herein, is defined as largely but not necessarily wholly that which is specified. The term generally, as used herein, is defined as at least approaching a given state. The term deploying, as used herein, is defined as designing, building, shipping, installing and/or operating. The term means, as used herein, is defined as hardware, firmware and/or software for achieving a result. The term program or phrase computer program, as used herein, is defined as a sequence of instructions designed for execution on a computer system. A program, or computer program, may include a subroutine, a function, a procedure, an object method, an object implementation, an executable application, an applet, a servlet, a source code, an object code, a shared library/dynamic load library and/or other sequence of instructions designed for execution on a computer or computer system.

All the disclosed embodiments of the invention disclosed herein can be made and used without undue experimentation in light of the disclosure. The invention is not limited by theoretical statements recited herein. Although the best mode of carrying out the invention contemplated by the inventor(s) is disclosed, practice of the invention is not limited thereto. Accordingly, it will be appreciated by those skilled in the art that the invention may be practiced otherwise than as specifically described herein.

It will be manifest that various substitutions, modifications, additions and/or rearrangements of the features of the invention may be made without deviating from the spirit and/or scope of the underlying inventive concept. It is deemed that the spirit and/or scope of the underlying inventive concept as defined by the appended claims and their equivalents cover all such substitutions, modifications, additions and/or rearrangements. All the disclosed elements and features of each disclosed embodiment can be combined with, or substituted for, the disclosed elements and features of every other disclosed embodiment except where such elements or features are mutually exclusive.

Variation may be made in the steps or in the sequence of steps composing methods described herein. Although the device(s) described herein can be a separate module, it will be manifest that the device(s) may be integrated into the system with which it is (they are) associated.

The individual components need not be formed in the disclosed shapes, or combined in the disclosed configurations, but could be provided in virtually any shapes, and/or combined in virtually all configurations. The individual components need not be fabricated from the disclosed materials, but could be fabricated from virtually any suitable materials.

Homologous replacements may be substituted for the substances described herein. Agents which are both chemically and physiologically related may be substituted for the agents described herein where the same or similar results would be achieved.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

REFERENCES

1. Endy D, Brent R 2001 Modelling cellular behaviour *Nature* 409 391-395
2. Hasty J, McMillen D, Collins J J 2002 *Nature* 420 224-230
3. Gardner T S, Cantor C R, Collins J J 2000 Construction of a genetic toggle switch in *Escherichia coli Nature* 403 339-342
4. Elowitz M B, Leibler S 2000 A synthetic oscillatory network of transcriptional regulators *Nature* 403 335-338
5. Guet C C, Elowitz M B, Hsing W H, Leibler S 2002 Combinatorial synthesis of genetic networks *Science* 296 1466-1470
6. Simpson M L, Sayler G S, Fleming J T, Applegate B 2001 Whole cell biocomputing *Trends in Biotechnology* 19 317-323
7. Chan W C W, Nie S M 1998 Quantum dot bioconjugates for ultrasensitive nonisotopic detection *Science* 281 2016-2018
8. Bruchez M, Moronne M, Gin P, Weiss S, Alivisatos A P 1998 Semiconductor nanocrystals as fluorescent biological labels *Science* 281 2013-2016
9. Dubertret B, Skourides P, Norris D J, Noireaux V, Brivanlou A H, Libchaber A 2002 In vivo imaging of quantum dots encapsulated in phospholipid micelles *Science* 298 17591762
10. Wightman R M, Jankowski J A, Kennedy R T, Kawagoe K T, Schroeder T J, Leszczyszyn D J, Near J A, Diliberto E J, Viveros O H 1991 Temporally resolved catecholamine spikes correspond to single vesicle release from individual chromaffin cells *Proc. Natl. Acad. Sci. U.S.A.* 88 10754-10758
11. Knoblauch M, Hibberd J M, Gray J C, van Bel A J E 1999 A galinstan expansion femtosyringe for microinjection of eukaryotic organelles and prokaryotes *Nature Biotechnol.* 17 906-909
12. McAllister D V, Allen M G, Prausnitz M R 2000 Microfabricated microneedles for gene and drug delivery *Annu. Rev. Biomedical Engin.* 2 289-313
13. Wong S S, Joselevich E, Woolley A T, Cheung C L, Lieber C M 1998 Covalently functionalized nanotubes as nanometer-sized probes in chemistry and biology *Nature* 394 52-55
14. Woolley A T, Guillemette C, Cheung C L, Housman D E, Lieber C M 2000 Direct haplotyping of kilobase-size DNA using carbon nanotube probes *Nature Biotechnol.* 18 760-763
15. Guillorn M A, McKnight T E, Melechko A V, Merkulov V I, Britt P F, Austin D W, Lowndes D H, Simpson M L 2002 Individually addressable vertically aligned carbon nanofiber-based electrochemical probes *J. Appl. Phys.* 91 3824-3828
16. Kim P, Lieber C M 1999 Nanotube Tweezers *Science* 286 2148-2150
17. Ren Z F, Huang Z P, Xu J W, Wang J H, Bush P, Siegal M P, Provencio P N 1998 Synthesis of large arrays of well-aligned carbon nanotubes on glass *Science* 282 1105-1107
18. Merkulov V I, Lowndes D H, Wei Y Y, Eres G, Voelkl E 2000 Patterned growth of individual and multiple vertically aligned carbon nanofibers *Appl. Phys. Lett.* 76 3555-3557
19. Merkulov V I, Guillorn M A, Lowndes D H, Simpson M L, Voelkl E 2001 Shaping carbon nanostructures by controlling the synthesis process *Appl. Phys. Lett.* 79 1178-1180
20. Cong B, Liu J, Tanksley S D 2002 Natural alleles at a tomato fruit size quantitative trait locus differ by heterochronic regulatory mutations *Proc. Natl. Acad. Sci. U.S.A.* 99 13606-13611
21. Dwyer C, Guthold M, Falvo M, Washburn S, Superfine R, Erie D 2002 DNA-functionalized single-walled carbon nanotubes *Nanotechnology* 13 601-604

22. Nguyen C V, Delzeit L, Cassell A M, Li J, Han J, Meyyappan M 2002 *Nano Letters* 2 1079-1081
23. Hsie A W, Casciano D A, Couch D B, Krahn D F, Oneill J P, Whitfield B L 1981 The use of chinese-hamster ovary cells to quantify specific locus mutation and to determine mutagenicity of chemicals—a report of the gene tox program *Mutat. Res.* 86 193-214
24. Merkulov V I, Melechko A V, Guillorn M A, Lowndes D H, Simpson M L 2002 Effects of spatial separation on the growth of vertically aligned carbon nanofibers produced by plasma-enhanced chemical vapor deposition *Appl. Phys. Lett.* 80 476-478
25. Brown G M, Allison D P, Warmack R J, Jacobson K B, Larimer F W, Woychik R P, Carrier W L 1991 Electrochemically induced adsorption of radiolabelled DNA on gold and HOPG substrates for STM investigations *Ultramicroscopy* 38 253-264
26. Hamad-Schifferli K, Schwartz J J, Santos A T, Zhang S G, Jacobson J M 2002 Remote electronic control of DNA hybridization through inductive coupling to an attached metal nanocrystal antenna *Nature* 415 152-155
27. Luo D, Saltzman W M 2000 Synthetic DNA delivery systems *Nature Biotechnol.* 18 33-37.
28. Filion M C, Phillips N C 1998 Major limitations in the use of cationic liposomes for DNA delivery *Int. J. Pharm.* 162 159-170
29. Merkulov, V. I., Melechko, A. V., Guillorn, M. A., Simpson, M. L., and Lowndes, D. H., Alignment mechanism of carbon nanofibers by plasma-enhanced chemical vapor deposition, Applied Physics Letters, Vol 79 No 18, 2970-2972, 29 Oct. 2001
30. Arbault S, Pantano P, Sojic N, Amatore C, Best-Belpomme M, Sarasin A, Vuillaume M, Activation of the NADPH oxidase in human fibroblasts by mechanical intrusion of a single cell with an ultramicroelectrode, Carcinogenesis (1997), vol 18, 569-574
31. Desai T A, Hansford D J, Ferrari M, Micromachined interfaces: new approaches in cell immunoisolation and biomolecular separation, BIOMOL ENG 17 (1): 23-36 October 2000
32. Merkulov V I, Lowndes D H, Baylor L R, Kang S, Field emission properties of different forms of carbon, SOLID-STATE ELECTRONICS, 45 (6): 949-956 June 2001
33. Ziauddin J and Sabatini D, Microarrays of cells expressing defined cDNAs, Nature (2001)

What is claimed is:

1. A method for expressing DNA in a cell, the method comprising:
   providing an elongated carbon nanofiber having a tip and having an expression vector DNA attached to at least a portion of the tip;
   penetrating the cell with the tip of said elongated carbon nanofiber and penetrating a nuclear membrane of the cell with the tip; and
   maintaining at least a portion of the tip containing said expression vector DNA within the nucleus of the cell while the expression vector DNA remains attached to the elongated carbon nanofiber, wherein said expression vector DNA is expressed in said cell, and
   removing said elongated carbon nanofiber bound to said expression vector DNA from the cell.

2. The method of claim 1, wherein a proximal end opposite the tip of the elongated carbon nanofiber is mechanically connected on a porous substrate that directs the flow of displaced cellular media when said carbon nanofiber has penetrated the membrane of the cell.

3. The method of claim 2, further comprising a metallized buffer layer between the porous substrate and the elongated carbon nanofiber.

4. The method of claim 1, further comprising culturing said cell.

5. The method of claim 1, wherein the DNA is complexed with a cationic agent to attach the DNA to the elongated carbon nanofiber.

6. The method of claim 5, wherein the cationic agent comprises spermidine.

7. The method of claim 1, wherein the tip of the elongated carbon nanofiber includes a metal catalyst selected from Ni, Co and/or Fe having an exposed portion on which the DNA is retained.

8. The method of claim 1, further comprising forming a metallization layer coupled to at least a portion of a surface of the tip of the elongated carbon nanofiber.

9. The method of claim 1, further comprising forming a silicon-containing oxide layer coupled to at least a portion of a surface of the tip of the elongated carbon nanofiber.

10. The method of claim 9, wherein the silicon-containing oxide layer is deposited by plasma enhanced chemical vapor deposition.

11. The method of claim 9, further comprising forming a hydrogel layer on the silicon containing oxide layer.

12. The method of claim 11, wherein the hydrogel layer is formed by polymerizing acrylimide and poly(n-isopropyl acrylamide).

13. The method of claim 1, further comprising forming a thermally reactive coating coupled to at least a portion of a surface of the tip of the elongated carbon nanofiber.

14. The method of claim 1, further comprising forming carboxylic acid groups on at least a portion of the tip of the elongated carbon nanofiber.

15. The method of claim 1, wherein the DNA is covalently bound to the elongated carbon nanofiber.

16. The method of claim 15, wherein the DNA is covalently bound by an EDC-mediated condensation reaction between carboxylic acid groups on the elongated carbon nanofiber and amino groups of the DNA.

17. The method of claim 1, wherein at least a portion of the tip of the elongated carbon nanofiber comprises a nitrogenated carbon composition.

* * * * *